United States Patent
Lawson et al.

(10) Patent No.: US 11,633,416 B1
(45) Date of Patent: Apr. 25, 2023

(54) ORAL FORMULATIONS OF CD73 COMPOUNDS

(71) Applicant: ARCUS BIOSCIENCES, INC., Hayward, CA (US)

(72) Inventors: Kenneth Victor Lawson, San Francisco, CA (US); Manmohan Reddy Leleti, Dublin, CA (US); Jay Patrick Powers, Pacifica, CA (US)

(73) Assignee: ARCUS BIOSCIENCES, INC., Hayward, CA (US)

( * ) Notice: Subject to any disclaimer, the term of this patent is extended or adjusted under 35 U.S.C. 154(b) by 0 days.

(21) Appl. No.: 17/193,473

(22) Filed: Mar. 5, 2021

Related U.S. Application Data

(60) Provisional application No. 62/986,453, filed on Mar. 6, 2020.

(51) Int. Cl.
| | |
|---|---|
| A61K 31/70 | (2006.01) |
| A01N 43/04 | (2006.01) |
| A61K 31/7064 | (2006.01) |
| A61K 47/24 | (2006.01) |
| A61K 9/00 | (2006.01) |

(52) U.S. Cl.
CPC ........ A61K 31/7064 (2013.01); A61K 9/0053 (2013.01); A61K 47/24 (2013.01)

(58) Field of Classification Search
None
See application file for complete search history.

(56) References Cited

U.S. PATENT DOCUMENTS

| | | | |
|---|---|---|---|
| 5,211,940 | A | 5/1993 | Ishiguro et al. |
| 5,211,956 | A | 5/1993 | Sawai et al. |
| 5,569,650 | A | 10/1996 | Watanabe et al. |
| 5,658,890 | A | 8/1997 | Pankiewicz et al. |
| 5,700,786 | A | 12/1997 | Watanabe et al. |
| 6,713,623 | B2 | 3/2004 | Pankiewicz et al. |
| 8,778,912 | B2 | 7/2014 | Freixedas et al. |
| 9,090,697 | B2 | 7/2015 | Sim |
| 10,239,912 | B2 | 3/2019 | Debien et al. |
| 10,981,944 | B2 | 4/2021 | Debien et al. |
| 11,001,603 | B2 | 5/2021 | Debien et al. |
| 2013/0022645 | A1 | 1/2013 | Son et al. |
| 2016/0000909 | A1 | 1/2016 | Eisenbach-Schwartz et al. |
| 2020/0405629 | A1 | 12/2020 | Jaen et al. |
| 2021/0177876 | A1 | 6/2021 | Ikenaga et al. |
| 2021/0371449 | A1 | 12/2021 | Debien et al. |
| 2021/0395291 | A1 | 12/2021 | Pennell et al. |
| 2022/0062313 | A1 | 3/2022 | Jeffrey et al. |

FOREIGN PATENT DOCUMENTS

| | | |
|---|---|---|
| WO | 1998/015563 A1 | 4/1998 |
| WO | 2002/048165 A2 | 6/2002 |
| WO | WO-2006017852 | 2/2006 |
| WO | WO-2007093611 | 8/2007 |
| WO | WO-2008082658 | 7/2008 |
| WO | WO-2010110923 | 9/2010 |
| WO | 2012/032513 A1 | 3/2012 |
| WO | WO-2012051568 | 4/2012 |
| WO | WO-2012156527 | 10/2013 |
| WO | WO-2015049447 | 4/2015 |
| WO | 2015/164573 A1 | 10/2015 |
| WO | 2017/029601 A1 | 2/2017 |
| WO | 2017/118689 A1 | 7/2017 |
| WO | 2017/120422 A1 | 7/2017 |
| WO | 2017/120508 A1 | 7/2017 |
| WO | WO-2019007929 | 1/2019 |
| WO | WO-2019201701 | 10/2019 |
| WO | WO-2020101302 | 5/2020 |
| WO | WO-2020141828 | 7/2020 |
| WO | WO-2021230600 | 11/2021 |
| WO | WO-2022132781 | 6/2022 |

OTHER PUBLICATIONS

Bowman, Christine E., et al. "An exceptionally potent inhibitor of human CD73." Biochemistry 58.31 (2019): 3331-3334.*
Ripphausen, Peter, et al. "Virtual screening identifies novel sulfonamide inhibitors of ecto-5'-nucleotidase." Journal of Medicinal Chemistry 55.14 (2012): 6576-6581.*
U.S. Appl. No. 17/311,945, filed Jun. 8, 2021, Jeffrey et al..
U.S. Appl. No. 17/348,833, filed Jun. 16, 2021, Pennell et al..
International Search Report and Written Opinion dated Apr. 19, 2017 corresponding to International Patent Application No. PCT/US2017/012587 filed on Jan. 6, 2017, 11 pages.
International Preliminary Report on Patentability dated Jul. 19, 2018 corresponding to International Patent Application No. PCT/US2017/012587 filed on Jan. 6, 2017, 7 pages.
Partial supplementary European Search Report dated Aug. 23, 2019 corresponding to EP Application No. 17736459.3 filed Jan. 6, 2017; 15 pages.
Extended European Search Report dated Nov. 28, 2019 corresponding to EP Application No. 17736459.3 filed Jan. 6, 2017; 11 pages.

(Continued)

*Primary Examiner* — Patrick T Lewis
(74) *Attorney, Agent, or Firm* — Sheppard Mullin Richter & Hampton LLP

(57) ABSTRACT

Oral formulations comprising a compound of Formula (I) and a chelating agent are provided, wherein compounds of Formula (I) have the structure:

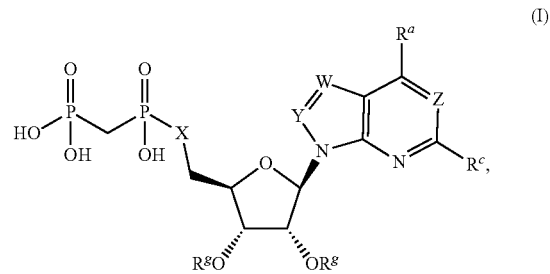

wherein, W, X, Y, Z, $R^a$, $R^c$, and each $R^g$ are as defined herein. Also provided are methods of preparation, methods of use, and specific dosage forms.

24 Claims, 2 Drawing Sheets

(56) References Cited

OTHER PUBLICATIONS

Al-Izki, Sarah et al., "Immunosuppression with FTY720 is insufficient to prevent secondary progressive neurodegeneration in experimental autoimmune encephalomyelitis," *Multiple Sclerosis Journal* (2011; accepted Jan. 21, 2011) 17(8):939-948.

Bhattarai, Sanjay et al., "α,β-Methylene-ADP (AOPCP) Derivatives and Analogues: Development of Potent and Selective ecto-5'-Nucleotidase (CD73) Inhibitors," *J. Med. Chem.* (Jul. 6, 2015) 58:6248-6263.

Furtmann, Norbert et al., "Evaluation of molecular model-based discovery of ecto-5'-nucleotidase inhibitors on the basis of X-ray structures," *Bioorganic & Medicine Chemistry* (Aug. 17, 2013) 21(21):6616-6622.

Lesiak, Krystyna et al., Synthesis of 2'-Deoxynucleoside 5'-Methylenebis-(Phosphonates)s Using 2-(4-Nitrophenyl)Ethyl Methylene-Bis(Phosphonate) as the Phosphonylating Agent, Nucleosides & Nucleotides, 1998, 17(9-11), pp. 1857-1860.

Kulesskaya, Natalia et al., "CD73 Is a Major Regulator of Adenosinergic Signalling in Mouse Brain," *PLOS ONE* (Jun. 12, 2013) 8(6):e66896; 12 pages.

Maruoka, Hiroshi et al., "Pyrimidine Ribonucleotides with Enhanced Selectivity as $P2Y_6$ Receptor Agonists: Novel 4-Alkyloxyimino, (S)-Methanocarba, and 5'-Triphosphate γ-Ester Modifications," *J. Med. Chem.* (2010;Published on Web May 6, 2010) 53(11):4488-4501.

Stagg, John et al., "Anti-CD73 antibody therapy inhibits breast tumor growth and metastasis", *PNAS*, (Jan. 26, 2010) 107(4):1547-1552; *This article has supporting information online at www.pnas.org/cgi/content/full/0908801107/DCSupplemental.

Webster, Rachel M., "The immune checkpoint inhibitors: where are we now?" *Nature Reviews* (Dec. 2014; published online Oct. 27, 2014) 13:883-884.

Zhenchuk, Anna et al., "Mechanisms of anti-cancer action and pharmacology of clofarabine," *Biochemical Pharmacology* (2009; accepted Jun. 23, 2009) 78:1351-1359.

Ashok D. et al., SITC 2019 Poster P379, Phase 1 Safety Study in Healthy Volunteers of AB680, a Small-Molecule Inhibitor of CD73 and Rationale for Combination Therapy in Patients with Gastrointestinal Malignancies, Nov. 7-10, 2019.

* cited by examiner

ORAL FORMULATIONS OF CD73 COMPOUNDS

CROSS-REFERENCES TO RELATED APPLICATIONS

This application claims priority benefit under 35 U.S.C. § 119(e) from U.S. Provisional No. 62/986,453, filed Mar. 6, 2020, which is hereby incorporated by reference in its entirety for all purposes.

BACKGROUND OF THE DISCLOSURE

Ectonucleotides catalyze the conversion of ATP to adenosine, an endogenous modulator that impacts multiple systems, including the immune system, the cardiovascular system, the central nervous system, and the respiratory system. Adenosine also promotes fibrosis in a variety of tissues. In the first step of the production of adenosine, ectonucleoside triphosphate diphosphohydrolase 1 (EN-TPD1), also known as CD39 (Cluster of Differentiation 39), hydrolyzes ATP to ADP, and then ADP to AMP. In the next step, AMP is converted to adenosine by 5'-nucleotidase, ecto (NT5E or 5NT), also known as CD73 (Cluster of Differentiation 73).

The enzymatic activities of CD39 and CD73 play strategic roles in calibrating the duration, magnitude, and chemical nature of purinergic signals delivered to various cells (e.g., immune cells). Alteration of these enzymatic activities can change the course or dictate the outcome of several pathophysiological events, including cancer, autoimmune diseases, infections, atherosclerosis, and ischemia-reperfusion injury, suggesting that these ecto-enzymes represent novel therapeutic targets for managing a variety of disorders.

The CD73 inhibitors in clinical development have been antibodies, as the development of small molecules has been hampered due to, for example, less than ideal metabolic stability, as well as the availability of suitable oral formulations that can effectively deliver the agent.

In view of the role played by CD73 in cancer, as well as a diverse array of other diseases, disorders and conditions, and the current lack of effective oral formulations of CD73 inhibitors available to medical practitioners, there is a need for such compositions and methods associated therewith.

BRIEF SUMMARY OF THE DISCLOSURE

In one aspect, provided herein are oral formulations comprising a compound of Formula (I) and a chelating agent, wherein the compound of Formula (I) has the structure:

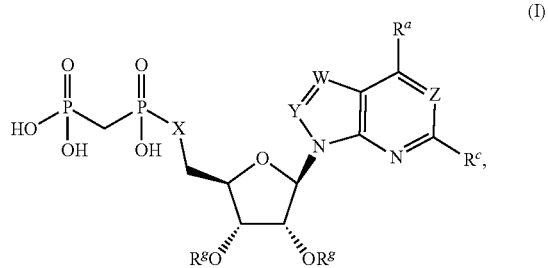

(I)

wherein, W, X, Y, Z, $R^a$, $R^c$, and each $R^g$ are as defined herein. Also provided are methods of preparation, methods of use, and dosage forms as described in detail below.

In one particular aspect, the present disclosure provides an oral formulation of a compound of Formula (I), wherein the compound of Formula (I) has the structure of Compound (Ia):

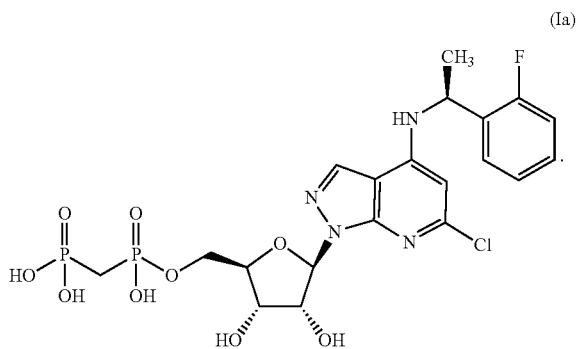 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

(Ia)

As noted above, the present disclosure also relates to the use of the oral formulations of such a compound for the treatment and/or prevention of an array of diseases, disorders and conditions mediated, in whole or in part, by CD73. CD73 inhibitors have been linked to the treatment of a diverse array of disorders, including cancer, fibrosis, neurological and neurodegenerative disorders (e.g., depression and Parkinson's disease), cerebral and cardiac ischemic diseases, immune-related disorders, and disorders with an inflammatory component. See, e.g., Sorrentino et al (2013) OncoImmunol, 2:e22448; and Regateiro et al. (2012) Clin. Exp. Immunol, 171:1-7. In particular embodiments, the oral formulations described herein can inhibit the immunosuppressive activity and/or the anti-inflammatory activity of CD73, and are useful as therapeutic or prophylactic therapy when such inhibition is desired. Unless otherwise indicated, when uses refer to a compound (or to the oral formulation of the compound) described herein, it is to be understood that such compound may be in any solid form (crystalline, amorphous or mixtures thereof) and/or to the compound as formulated.

In some embodiments, the present disclosure contemplates methods for treating or preventing cancer in a subject (e.g., a human) comprising administering to the subject a therapeutically effective amount of an oral formulation comprising a compound of Formula (I) and a chelating agent. The present disclosure includes methods of treating or preventing a cancer in a subject by administering to the subject the oral formulation in an amount effective to reverse, stop or slow the progression of CD73-mediated immunosuppression.

Examples of the cancers that can be treated using the oral formulation comprising a compound of Formula (I) and a chelating agent include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present disclosure, the cancer is melanoma, colon cancer, pancreatic cancer, breast cancer, prostate cancer, lung cancer, leukemia, a brain tumor, lymphoma, sarcoma, ovarian cancer, or Kaposi's sarcoma. Cancers that are candidates for treatment with an oral formulation comprising a compound of Formula (I) and a chelating agent are discussed further hereafter.

The present disclosure contemplates methods of treating a subject receiving a bone marrow transplant, peripheral blood stem cell transplant or other types of transplants by administering a therapeutically effective amount of an oral formulation comprising a compound of Formula (I) and a chelating agent sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present disclosure contemplates methods for treating or preventing an infective disorder (e.g., a viral infection) in a subject (e.g., a human) comprising administering to the subject a therapeutically effective amount of an oral formulation comprising a compound of Formula (I) and a chelating agent. In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, the present disclosure contemplates methods for treating and/or preventing immune-related diseases, disorders and conditions; diseases having an inflammatory component; as well as disorders associated with the foregoing; with an oral formulation comprising a compound of Formula (I) and a chelating agent. Examples of immune-related diseases, disorders and conditions are described hereafter.

Other diseases, disorders and conditions that can be treated or prevented, in whole or in part, by modulation of CD73 activity are candidate indications for an oral formulation comprising a compound of Formula (I) and a chelating agent as described herein.

The present disclosure further contemplates the use of the oral formulation comprising a compound of Formula (I) and a chelating agent described herein in combination with one or more additional agents. The one or more additional agents may have some CD73-modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the oral formulation comprising a compound of Formula (I) and a chelating agent and one or more additional agent(s) may be in the form of a single composition or multiple compositions, and the treatment modalities can be administered concurrently, sequentially, or through some other regimen. By way of example, the present disclosure contemplates a treatment regimen wherein a radiation phase is followed by a chemotherapeutic phase. The combination therapy can have an additive or synergistic effect. Other benefits of combination therapy are described hereafter.

DETAILED DESCRIPTION OF THE DISCLOSURE

Figure 1:
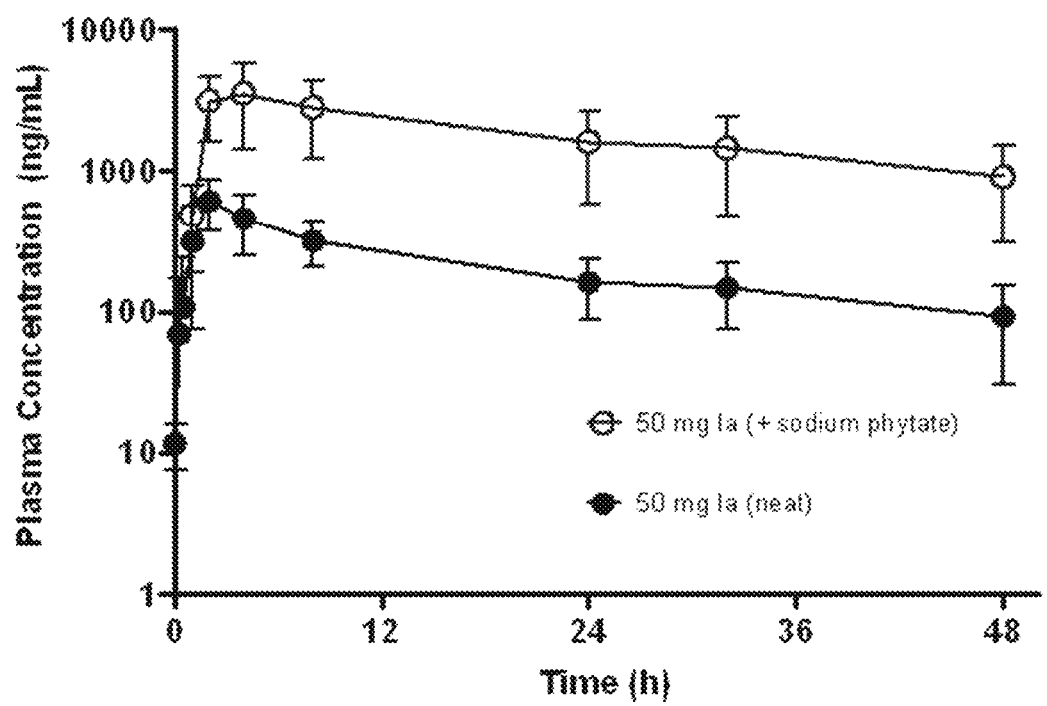
FIG. 1 shows a 48 hour time course of plasma concentration for Compound (Ia) (neat) and in combination with sodium phytate (i.e., inositol hexaphosphate sodium salt).
Figure 2:
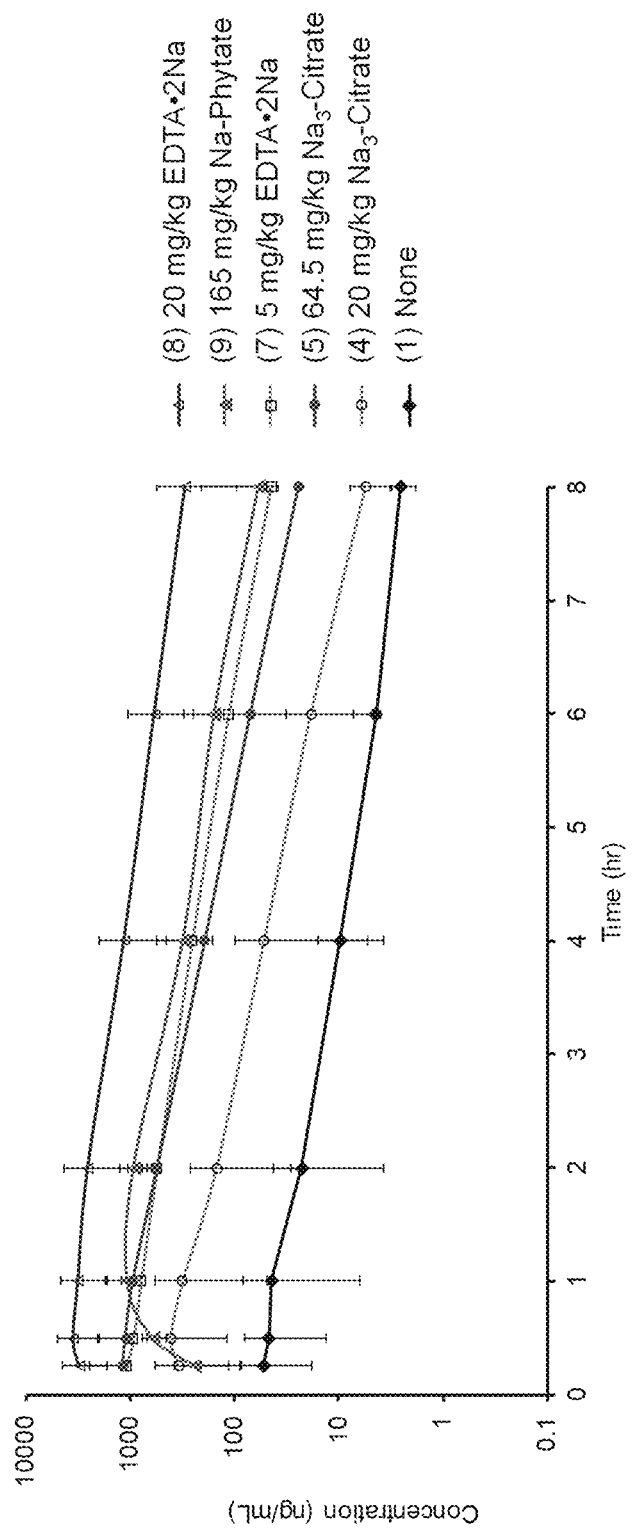
FIG. 2 shows an 8 hour time course of plasma concentration for Compound 2 dosed neat (bottom), or dosed with 20 mg/kg trisodium citrate (second from bottom), 64.5 mg/kg trisodium citrate (third from bottom), 5 mg/kg sodium EDTA (third from top), 165 mg/kg sodium phytate (second from top), or 20 mg/kg sodium EDTA (top).

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure. Unless defined otherwise, all technical and scientific terms used herein have the same meaning as commonly understood by one of ordinary skill in the art to which this disclosure belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

The present disclosure is directed to oral formulations of CD73 inhibitors (e.g., compounds of Formula (I), or other nucleoside or nucleotide compounds) in combination with a chelating agent. Surprisingly, the noted combination provides improved oral bioavailability of CD73 inhibitors. In some embodiments, the compound of Formula (I) is (((((2R, 3S,4R,5R)-5-(6-chloro-4-(((S)-1-(2-fluorophenyl)ethyl) amino)-1H-pyrazolo[3,4-b]pyridin-1-yl)-3,4-dihydroxytetrahydrofuran-2-yl)methoxy)(hydroxy)phosphoryl)methyl) phosphonic acid, shown below as Compound (Ia):

Compound (Ia)

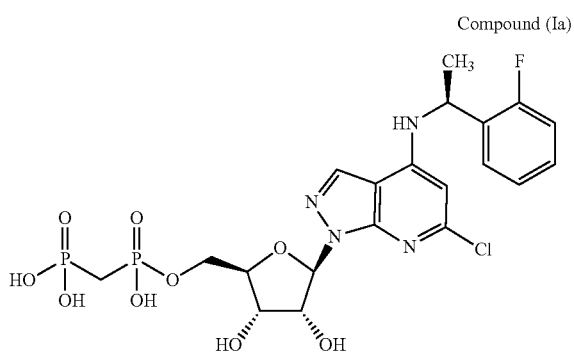 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

Definitions

Unless otherwise indicated, the following terms are intended to have the meaning set forth below. Other terms are defined elsewhere throughout the specification.

The term "alkyl", by itself or as part of another substituent, means, unless otherwise stated, a saturated straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "alkylene" refers to a straight or branched, saturated, aliphatic radical having the number of carbon atoms indicated, and linking at least two other groups, i.e., a divalent hydrocarbon radical. When two moieties are linked to the alkylene they can be linked to the same atom or different atoms of the alkylene group. For instance, a straight chain alkylene can be the bivalent radical of $(CH_2)_n$, where n is 1, 2, 3, 4, 5 or 6. Representative alkylene groups include, but are not limited to, methylene, ethylene, propylene, isopropylene, butylene, isobutylene, secbutylene, pentylene and hexylene.

The term "cycloalkyl" refers to a monocyclic, bicyclic or polycyclic non-aromatic hydrocarbon ring system having the indicated number of ring atoms (e.g., a $C_{3-6}$ cycloalkyl has from 3 to 6 ring carbon atoms). Cycloalkyl groups can be saturated or partially unsaturated, i.e., cycloalkyl groups can be characterized by one or more points of unsaturation, provided the points of unsaturation do not result in an aromatic system. Examples of monocyclic cycloalkyl groups include, but are not limited to, cyclopropyl, cyclobutyl, cyclopentyl, cyclohexyl, cyclohexeneyl, cycloheptyl, cyclooctyl, cyclootceneyl, cyclooctadienyl and the like. "Cycloalkyl" also refers to bicyclic and polycyclic hydrocarbon rings such as, for example, bicyclo[2.2.1]heptane, bicyclo[2.2.2]octane, etc. In some embodiments, the cycloalkyl compounds of the present disclosure are monocyclic $C_{3-6}$ cycloalkyl moieties.

The term "heterocycloalkyl" refers to a monocyclic, bicyclic or polycyclic cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

As used herein, a wavy line, "⁓", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible.

As referred to herein, divalent components include either orientation (forward or reverse) of that component. For example, the group "—C(O)NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "arylalkyl" and "heteroarylalkyl" are used in their conventional sense, and refer to those groups wherein an aryl group or a heteroaryl group is attached to the remainder of the molecule via $C_1$-$C_4$ alkylene linker. An exemplary embodiment of "arylalkyl" is phenylmethyl (or benzyl). Similarly, an exemplary embodiment of "heteroarylalkyl" is, for example, 3-pyridylpropyl. When 'optionally substituted' is used to describe either of the terms "arylalkyl" or "heteroarylalkyl", it is meant to refer to those groups wherein the aryl or heteroaryl portion is optionally substituted as in the definitions below, and the alkyl portion is optionally substituted as in the definitions below.

The terms "cycloalkylalkyl" and "heterocycloalkylalkyl" are used in their conventional sense, and refer to those groups wherein a cycloalkyl group or a heterocycloalkyl group is attached to the remainder of the molecule via a $C_1$-$C_4$ alkylene linker. An exemplary embodiment of a cycloalkyl$C_1$-$C_4$alkyl group is methylcyclopentane. An exemplary embodiment of a heterocycloalkyl$C_1$-$C_4$alkyl is 2-ethylpyrrolidine. When 'optionally substituted' is used to describe either of the terms "cycloalkyl$C_1$-$C_4$alkyl" and "heterocycloalkyl$C_1$-$C_4$alkyl", it is meant to refer to those groups wherein the cycloalkyl or heterocycloalkyl portion is optionally substituted as in the definitions below, and the alkyl portion is optionally substituted as in the definitions below.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl groups. For example, the term "$C_{1-4}$ haloalkyl" is meant to include trifluoromethyl, 2,2,2-trifluoroethyl, 4-chlorobutyl, 3-bromopropyl, and the like.

The term "aryl" means, unless otherwise stated, a polyunsaturated monocyclic, bicyclic or tricyclic aromatic hydrocarbon group. Bicyclic and tricyclic ring systems may be fused or linked covalently. Non-limiting examples of aryl groups include phenyl, naphthyl and biphenyl.

The term "heteroaryl" refers to monocyclic or fused bicyclic aromatic groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or a carbon atom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below. In some embodiments, the optionally substituted alkyl, aryl and heteroaryl groups are optionally substituted with 1-5 substituents as defined below. In some embodiments, the optionally substituted alkyl, aryl and heteroaryl groups are optionally substituted with 1-3 substituents as defined below.

Optional substituents for the alkyl radicals (including those groups often referred to as alkylene, alkenyl, alkynyl and cycloalkyl) can be a variety of groups selected from: halogen, —OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR"R", —NR'S(O)$_2$R", —CN and —NO$_2$ in a number ranging from zero to (2 m'+1), where m' is the total number of carbon atoms in such radical. R', R" and R"' each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR"R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-4 carbon atoms.

As used herein, the term "heteroatom" is meant to include oxygen (O), nitrogen (N), sulfur (S) and silicon (Si). In some embodiments, the heteroatom is oxygen or nitrogen.

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. Certain compounds of the present disclosure may exist in multiple crystalline or amorphous forms (see, e.g., WO 2020/123772). In general, all physical forms are contemplated by the present disclosure and are intended to be within the scope of the present disclosure.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium (2H) or carbon-13 ($^{13}$C). Such isotopic variations can provide additional utilities to those described elsewhere within this application. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure.

"Hydrate" refers to a complex formed by, for example, combining compounds of Formula (I) (CD73 inhibiting compounds) and water. The term includes stoichiometric as well as non-stoichiometric hydrates.

"Solvate" refers to a complex formed by the combining of compounds of Formula (I) and a solvent.

"Desolvated" refers to a compound of Formula (I) that is a solvate as described herein, and from which solvent molecules have been partially or completely removed. Desolvation techniques to produce desolvated forms include, without limitation, exposure of a compound of Formula (I) (solvate) to a vacuum, subjecting the solvate to elevated temperature, exposing the solvate to a stream of gas, such as air or nitrogen, or any combination thereof. Thus, a desolvated compound of Formula (I) form can be completely without solvent molecules, or partially solvated wherein solvent molecules are present in stoichiometric or non-stoichiometric amounts.

"Alcohol" refers to a solvent having a hydroxy group. Representative alcohols can have any suitable number of carbon atoms, such as $C_1$-$C_6$, and any suitable number of hydroxy groups, such as 1-3. Exemplary alcohols include, but are not limited to, methanol, ethanol, n-propanol, isopropanol, etc.

The terms "patient" or "subject" are used interchangeably to refer to a human or a non-human animal (e.g., a mammal).

The term "oral administration" as used herein refers to a route of administration of a pharmaceutical formulation by mouth. Absorption of the therapeutic agent by way of oral administration can occur in the oral cavity (e.g., buccal or lingual absorption), or in the gastrointestinal tract. Pharmaceutical compositions intended for oral administration can be formulated as a liquid, solution, tablet, capsule, lozenge, troche, suspension, emulsion, syrup, elixir, or other forms suitable to administered by the mouth.

The terms "treat", "treating", treatment" and the like refer to a course of action (such as administering an inhibitor of CD73 or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an CD73 inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent (i.e., a compound of Formula (I)) to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an CD73 inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a patient-reported outcome).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of a particular biomolecule, e.g., CD73, either directly or indirectly.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

As used herein, "nucleobase" refers to a naturally occurring nucleobase or a modified nucleobase. Naturally occurring nucleobases include adenine (A), thymine (T), cytosine (C), uracil (U), and guanine (G). Modified nucleobases include compounds where one or more nitrogen atoms in a natural nucleobase are replaced with a carbon atom, one or more carbon atoms in a natural nucleobase are replaced with a nitrogen atom, one or more additional substituents are attached to the nucleobase, or combinations thereof. Non limiting examples of modified nucleobases include, but are not limited to, optionally substituted pyrazolopyrimidine, optionally substituted pyrrolopyridine and optionally substituted pyrazolopyridine. Optional substituents include, but are not limited to, halogens, amino groups, phenyl groups, benzyl groups. Further exemplary additional substituents include, $R^a$, $R^b$, $R^c$, $R^d$, and $R^e$, wherein $R^a$ is selected from the group consisting of H, $NH_2$, $NHR^7$, $NHC(O)R^7$, $NR^7R^7$, $R^7$, OH, $SR^7$ and $OR^7$; $R^b$ is selected from the group consisting of H, halogen, $NH_2$, $NHR^7$, $NR^7R^7$, $R^7$, OH, and $OR^7$; $R^c$ and $R^d$ are independently selected from the group consisting of H, halogen, haloalkyl, $NH_2$, $NHR^7$, $NR^7R^7$, $R^7$, OH, $OR^7$, $SR^7$, $SO_2R^7$, $-X^1-NH_2$, $-X^1-NHR^7$, $-X^1-NR^7R^7$, $-X^1-OH$, $-X^1-OR^7$, $-X^1-SR^7$ and $-X^1-SO_2R^7$; $R^e$ and $R^f$ are independently selected from the group consisting of H, halogen, and optionally substituted $C_1$-$C_6$ alkyl; each $X^1$ is $C_1$-$C_4$alkylene; and each $R^7$ is independently selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_7$ cycloalkyl, optionally substituted $C_3$-$C_7$ cycloalkyl$C_1$-$C_4$alkyl-, optionally substituted 4-7 membered cycloheteroalkyl, optionally substituted 4-7 membered cycloheteroalkyl$C_1$-$C_4$alkyl-, optionally substituted aryl, optionally substituted aryl$C_1$-$C_4$alkyl-, optionally substituted aryl$C_2$-$C_4$alkenyl-, optionally substituted aryl$C_2$-$C_4$alkynyl-, optionally substituted heteroaryl, optionally substituted heteroaryl$C_1$-$C_4$alkyl-, optionally substituted heteroaryl$C_1$-$C_4$alkenyl-, optionally substituted heteroaryl$C_2$-$C_4$alkynyl-, and optionally, two $R^7$ groups attached to a nitrogen atom are joined together to form a 4- to 7-membered heterocyclic ring, optionally fused to an aryl ring. A review of the compounds disclosed herein will further illuminate the modified nucleobases within the scope of the present application.

As used herein, "nucleoside" refers to a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety (e.g., a modified ribose moiety). Modification to the sugar moiety includes, but is not limited to, removal of one or more hydroxyl moieties, replacement of one or more hydroxyl moieties with a halogen, an $C_{1-4}$ alkyl, or a $C_{1-4}$ alkoxy, as well as addition of a halogen, $C_{1-4}$ alkyl, or a $C_{1-4}$ alkoxy to the sugar moiety.

As used herein, the term "nucleotide" refers to a nucleoside linked to a mono, di, or tri, phosphate or a derivative thereof. Derivatives of phosphate include thiophosphates (where one or more phosphate groups includes one or more sulfur atoms replace an oxygen atom), one or more phosphonate linkages (where the linking oxygen between two phosphates is replaced with an optionally substituted methylene group), as well as prodrug forms of the same. Prodrug forms of phosphates and derivatives thereof are known in the art and include alkyl esters, benzyl esters, aryl esters, alkoxycarbonyloxymethyl esters, as well as phosphoramidite esters. A review of the compounds disclosed herein will further illuminate the phosphates and derivatives thereof within the scope of the present application.

As used herein, the term "α" (alpha) in the context of substituents attached to the nucleoside sugar moiety refers to a given substituent being on the opposite side of the ring as the nucleobase. In the classic representation of ribose nucleosides, an α substituent results in a "downward projection," while the nucleobase is shown with an "upward projection." As a non-limiting example, a 2'-α fluoro substituent on a ribose nucleoside is shown below:

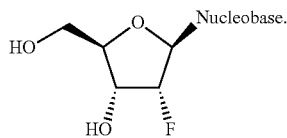

As used herein, the term "β" (beta) in the context of substituents attached to the nucleoside sugar moiety refers to a given substituent being on the same side of the ring as the nucleobase. In the classic representation of ribose nucleosides, a β substituent results in a "upward projection" while the nucleobase is also shown with an "upward projection." As a non-limiting example, a 2'-β fluoro substituent on a ribose nucleoside is shown below:

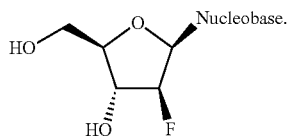

Oral Formulations

In one aspect, provided herein are oral formulation comprising a compound of Formula (I) or a pharmaceutically acceptable salt, hydrate or solvate thereof, and a chelating agent, wherein the compound of Formula (I) has the structure:

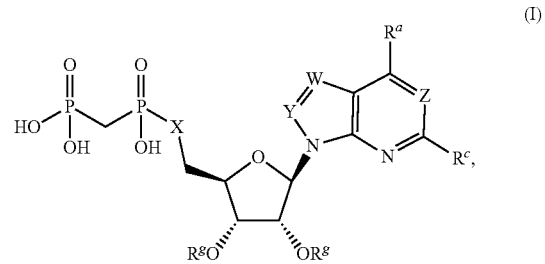

wherein, W, X, Y, Z, $R^a$, $R^c$, and each $R^g$ are as defined herein. In one or more embodiments, the chelating agent is edetic acid (EDTA), egtazic acid (EGTA), citric acid, polystyrene sulfonic acid, phosphoric acid, inositol hexaphosphate or an ionized salt of any of the foregoing. In some embodiments, the chelating agent is inositol hexaphosphate or an ionized salt thereof. In some embodiments, the chelating agent is edetic acid (EDTA) or an ionized salt thereof.

Compounds of Formula (I)

The oral formulations described herein are useful for delivery of compounds of Formula (I)

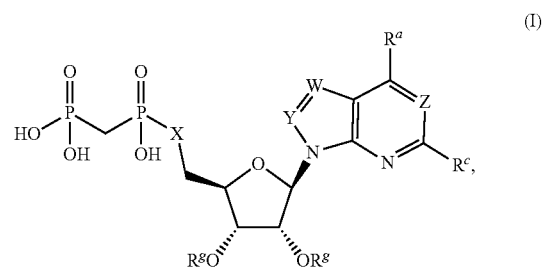

or a pharmaceutically acceptable salt, hydrate or solvate thereof, wherein,

W is selected from the group consisting of $CR^e$ and N;
X is selected from the group consisting of O, $CH_2$, and S;
each of Y and Z is independently selected from the group consisting of CH and N;
$R^g$ is H or the two $R^g$ groups are combined to form an acetonide;
$R^a$ is selected from the group consisting of $NH_2$, $NHR^1$ and $NRR^2$;
$R^c$ is selected from the group consisting of H, halogen, haloalkyl, $NH_2$, $NHR^3$, $NR^3R^4$, $R^3$, OH, $OR^3$, $SR^3$, $SO_2R^3$, —$X^1$—$NH_2$, —$X^1$—$NHR^3$, —$X^1$—$NR^3R^4$, —$X^1$—OH, —$X^1$—$OR^3$, —$X^1$—$SR^3$ and —$X^1$—$SO_2R^3$;
$R^e$ is selected from the group consisting of H, halogen, and optionally substituted $C_1$-$C_6$ alkyl;
each $X^1$ is $C_1$-$C_4$alkylene; and
each $R^1$, $R^2$, $R^3$, and $R^4$ is independently selected from the group consisting of optionally substituted $C_1$-$C_{10}$ alkyl, optionally substituted $C_3$-$C_7$ cycloalkyl, optionally substituted $C_3$-$C_7$ cycloalkyl$C_1$-$C_4$alkyl, optionally substituted 4-7 membered heterocycloalkyl, optionally substituted 4-7 membered heterocycloalkyl$C_1$-$C_4$alkyl, optionally substituted aryl, optionally substituted aryl$C_1$-$C_4$alkyl, optionally substituted heteroaryl, optionally substituted heteroaryl$C_1$-$C_4$alkyl, or when $R^1$ and $R^2$ or $R^3$ and $R^4$ are attached to the same nitrogen, they combine to form a 4- to 7-membered heterocyclic ring.

In some embodiments, the compound of Formula (I), useful in the formulations described herein is the compound wherein X is O.

In some embodiments, the compound of Formula (I), useful in the formulations described herein is the compound wherein each $R^9$ is H.

In some embodiments, the compound of Formula (I), useful in the formulations described herein is the compound of any embodiments above, wherein $R^a$ is $NHR^1$ and $R^1$ is selected from the group consisting of optionally substituted aryl$C_1$-$C_4$alkyl- and optionally substituted heteroaryl$C_1$-$C_4$alkyl-. In some embodiments the optionally substituted aryl$C_1$-$C_4$alkyl- and optionally substituted heteroaryl$C_1$-$C_4$alkyl- are optionally substituted with 1-3 halo. In some embodiments, the optionally substituted aryl$C_1$-$C_4$alkyl- and optionally substituted heteroaryl$C_1$-$C_4$alkyl- are optionally substituted with 1 fluoro.

In some embodiments, the compound of Formula (I), useful in the formulations described herein is the compound of any embodiments above, wherein $R^a$ is $NHR^1$ and $R^1$ is optionally substituted aryl$C_1$-$C_4$alkyl-. In some embodiments the optionally substituted aryl$C_1$-$C_4$alkyl- is optionally substituted with 1-3 halo. In some embodiments the optionally substituted aryl$C_1$-$C_4$alkyl- is optionally substituted with 1 fluoro.

In some embodiments, the compound of Formula (I), useful in the formulations described herein is the compound of any embodiments above, wherein $R^c$ is selected from the group consisting of H, halogen, and haloalkyl.

In some embodiments, the compound of Formula (I), useful in the formulations described herein is the compound of any embodiments above, wherein $R^c$ is halogen.

In some embodiments, the compound of Formula (I), useful in the formulations described herein is the compound of any embodiments above, wherein $R^c$ is H.

In some embodiments, the compound of Formula (I), useful in the formulations described herein is a compound of Formula (II):

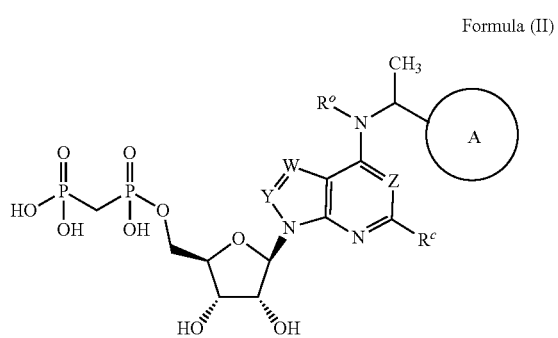

Formula (II)

or a pharmaceutically acceptable salt, hydrate or solvate thereof, wherein, $R^o$ is selected from the group consisting of H, optionally substituted $C_1$-$C_{10}$ alkyl, optionally substituted $C_3$-$C_7$ cycloalkyl, optionally substituted $C_3$-$C_7$ cycloalkyl$C_1$-$C_4$alkyl, optionally substituted 4-7 membered heterocycloalkyl, optionally substituted 4-7 membered heterocycloalkyl$C_1$-$C_4$alkyl, optionally substituted aryl, optionally substituted aryl$C_1$-$C_4$alkyl, optionally substituted heteroaryl, optionally substituted heteroaryl$C_1$-$C_4$alkyl, or when $R^1$ and $R^2$ or $R^3$ and $R^4$ are attached to the same nitrogen, they combine to form a 4- to 7-membered heterocyclic ring;

A is an optionally substituted aryl or heteroaryl; and each of W, Y, Z, and $R^c$ are as defined in Formula (I).

In some embodiments comprising a compound of Formula (II), $R^o$ is selected from the group consisting of H and optionally substituted $C_1$-$C_4$ alkyl. In one or more embodiments, $R^o$ is H or methyl. In some embodiments, $R^o$ is H.

In one or more embodiments comprising a compound of Formula (II), $R^c$ is selected from the group consisting of H, halogen, and haloalkyl. In some embodiments, $R^c$ is H or halogen. In some embodiments, $R^c$ is chloro.

In one or more embodiments comprising a compound of Formula (II), $R^e$ is H.

In some embodiments, comprising a compound of Formula (II), A is an aryl or heteroaryl optionally substituted with 1-3 halogen. In one or more embodiments, A is phenyl optionally substituted with 1 fluoro.

In some embodiments, the compound of Formula (I) or Formula (II), useful in the formulations described herein is the compound having a structure selected from the group consisting of:

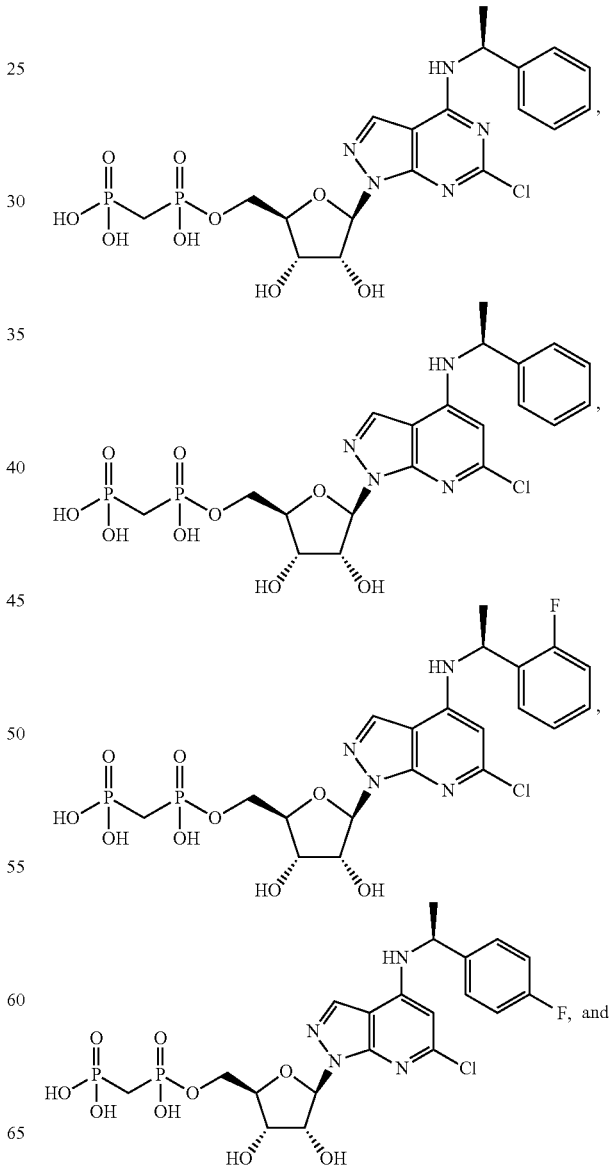

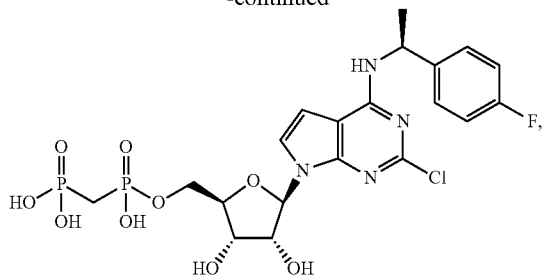

or a pharmaceutically acceptable salt thereof.

Inositol Hexaphosphate

The oral formulations provided herein comprise a chelating agent. In one or more embodiments, the chelating agent is inositol hexaphosphate or an ionized salt thereof (e.g., sodium phytate).

In some embodiments, the inositol hexaphosphate is a partially ionized salt thereof. In still further embodiments, the partially ionized salt is hexasodium inositol hexaphosphate.

In some embodiments, the partially ionized inositol hexaphosphate is an inositol hexaphosphate having not less than 4 mol sodium per mol of inositol phosphate. In other embodiments, the partially ionized inositol hexaphosphate is an inositol hexaphosphate having not less than 3 mol sodium per mol of inositol phosphate. In still other embodiments, the partially ionized inositol hexaphosphate is an inositol hexaphosphate having not less than 2 mol sodium per mol of inositol phosphate.

In some embodiments, the inositol hexaphosphate is a fully ionized salt thereof. In still other embodiments, the inositol hexaphosphate is dodecasodium inositol phosphate.

Formulations of a Nucleoside or Nucleotide Compound and Inositol Hexaphosphate or an Ionized Salt Thereof Also provided herein are oral formulations comprising a nucleoside or nucleotide compound and a chelating agent. In one or more embodiments, the chelating agent is inositol hexaphosphate or an ionized salt thereof (e.g., sodium phytate).

In some embodiments, the inositol hexaphosphate is a partially ionized salt thereof. In still further embodiments, the partially ionized salt is hexasodium inositol hexaphosphate.

In some embodiments, the partially ionized inositol hexaphosphate is an inositol hexaphosphate having not less than 4 mol sodium per mol of inositol phosphate. In other embodiments, the partially ionized inositol hexaphosphate is an inositol hexaphosphate having not less than 3 mol sodium per mol of inositol phosphate. In still other embodiments, the partially ionized inositol hexaphosphate is an inositol hexaphosphate having not less than 2 mol sodium per mol of inositol phosphate.

In some embodiments, the inositol hexaphosphate is a fully ionized salt thereof. In still other embodiments, the inositol hexaphosphate is dodecasodium inositol phosphate.

The formulations described herein can have different molar ratios of inositol hexaphosphate or an ionized salt thereof to nucleoside or nucleotide compound. In some embodiments, the molar ratio of inositol hexaphosphate or an ionized salt thereof to nucleoside or nucleotide compound in the formulation, for any of the embodiments above, is from about 1:1 to 10:1. In some embodiments, the molar ratio of inositol hexaphosphate or an ionized salt thereof to nucleoside or nucleotide compound in the formulation, for any of the embodiments above, is from about 3:1 to 10:1. In some embodiments, the molar ratio of inositol hexaphosphate or an ionized salt thereof to nucleoside or nucleotide compound in the formulation, for any of the embodiments above, is from about 4:1 to 7:1. In some embodiments, the molar ratio of inositol hexaphosphate or an ionized salt thereof to nucleoside or nucleotide compound in the formulation, for any of the embodiments above, is from about 5:1 to 6:1. In some embodiments, the molar ratio of inositol hexaphosphate or an ionized salt thereof to nucleoside or nucleotide compound in the formulation is about 5.5:1. In some embodiments, the molar ratio of inositol hexaphosphate or an ionized salt thereof to nucleoside or nucleotide compound in the formulation, for any of the embodiments above, is from about 1:1 to 7:1. In some embodiments, the molar ratio of inositol hexaphosphate or an ionized salt thereof to nucleoside or nucleotide compound in the formulation, for any of the embodiments above, is from about 1:1 to 5:1. In some embodiments, the molar ratio of inositol hexaphosphate or an ionized salt thereof to nucleoside or nucleotide compound in the formulation, for any of the embodiments above, is from about 2:1 to 4:1. In some embodiments, the molar ratio of inositol hexaphosphate or an ionized salt thereof to nucleoside or nucleotide compound in the formulation is about 3.5:1.

In some embodiments, the nucleoside or nucleotide compound comprises an optionally substituted adenosine nucleobase. In other embodiments, the nucleoside or nucleotide compound comprises an optionally substituted pyrrolopyrimidine nucleobase. In other embodiments, the nucleoside or nucleotide compound comprises an optionally substituted pyrazolopyrimidine nucleobase. In other embodiments, the nucleoside or nucleotide compound comprises an optionally substituted pyrrolopyridine nucleobase. In other embodiments, the nucleoside or nucleotide compound comprises an optionally substituted pyrazolopyridine nucleobase.

In other embodiments, the nucleoside or nucleotide compound comprises a ribose sugar moiety or a derivative thereof. In some embodiments, the nucleoside or nucleotide compound comprises a ribose sugar moiety. In some embodiments, the nucleoside or nucleotide compound comprises a ribose sugar moiety comprising a 2'-β methyl substituent. In other embodiments, the nucleoside or nucleotide compound comprises a 2'-deoxyribose sugar moiety. In still other embodiments, the nucleoside or nucleotide compound comprises a 2'-deoxy-2'-β-fluoro ribose sugar moiety. In still other embodiments, the nucleoside or nucleotide compound comprises a 3'-deoxy-ribose sugar moiety. In yet other embodiments, the nucleoside or nucleotide compound comprises a 2', 3'-dideoxy-ribose sugar moiety.

In some embodiments, the nucleoside or nucleotide compound is a nucleotide compound. In some embodiments, the nucleotide compound comprises a diphosphate group or a prodrug ester thereof. In some embodiments, the nucleotide compound comprises a triphosphate group or a prodrug ester thereof. In some embodiments, the nucleotide compound comprises a methylenebisphosphonate group or a prodrug ester thereof.

In certain embodiments, specific to those described above, the compound of Formula (I) or the nucleoside or nucleotide compound is an inhibitor of CD73.

Formulations of a CD73 Inhibiting Compound and a Chelating Agent

In a related aspect, provided herein is an oral formulation of a CD73 inhibiting compound and a chelating agent.

In some embodiments, the CD73 inhibiting compound is a compound of Formula (I) or a pharmaceutically acceptable salt, hydrate or solvate thereof, as described above, or a nucleoside or nucleotide compound, also as described above.

In some embodiments, the chelating agent is a calcium chelator. Without wishing to be bound by theory, chelating agents widen the tight junctions between epithelial cells in the gastrointestinal tract and facilitate the absorption of small molecules into systemic circulation. In some embodiments, the chelating agent is selected from the group consisting of edetic acid (EDTA), egtazic acid (EGTA), citric acid, polystyrene sulfonic acid, phosphonic acid, and inositol hexaphosphate or an ionized salt of any of the foregoing. In some embodiments, the chelating agent is selected from the group consisting of edetate disodium (sodium EDTA), egtazic acid sodium salt (sodium EGTA), trisodium citrate, sodium polystyrene sulfonate, sodium phosphate, and inositol hexaphosphate or an ionized salt thereof. In some embodiments, the chelating agent is edetic acid (EDTA) or an ionized salt thereof. In other embodiments, the chelating agent is inositol hexaphosphate or an ionized salt thereof.

5'-Nucleotidase, ecto and Inhibition Thereof

Human CD73 (also referred to as 5'-nucleotidase, ecto; NT5E; or 5NT) is a 574 amino acid residue protein (Accession No. AAH6593). Eukaryotic CD73 functions as a non-covalent homodimer with two structural domains, wherein the N- and C-terminal domains are connected by a hinge region that enables the enzyme to undergo large domain movements and switch between open and closed conformations (Knapp, K. et al. (2012) Structure 20:2161-73).

As used herein, the terms "CD73 inhibitor", "CD73 blocker", "adenosine by 5'-nucleotidase, ecto inhibitor", "NT5E inhibitor", "5NT inhibitor" and all other related art-accepted terms refer to a compound capable of modulating, either directly or indirectly, the CD73 receptor in an in vitro assay, an in vivo model, and/or other means indicative of therapeutic efficacy. The terms also refer to compounds that exhibit at least some therapeutic benefit in a human subject. An CD73 inhibitor may be a competitive, noncompetitive, or irreversible CD73 inhibitor. "A competitive CD73 inhibitor" is a compound that reversibly inhibits CD73 enzyme activity at the catalytic site; "a noncompetitive CD73 inhibitor" is a compound that reversibly inhibits CD73 enzyme activity at a non-catalytic site; and "an irreversible CD73 inhibitor" is a compound that irreversibly eliminates CD73 enzyme activity by forming a covalent bond (or other stable means of inhibiting enzyme function) with the enzyme.

CD73 inhibitors can modulate purinergic signaling, a type of extracellular signaling mediated by purine nucleotides and nucleosides such as ATP and adenosine. Purinergic signaling involves the activation of purinergic receptors in the cell and/or in nearby cells, resulting in the regulation of cellular functions. The enzymatic activity of CD73 plays a strategic role in calibrating the duration, magnitude, and chemical nature of purinergic signals delivered to various cells (e.g., immune cells). Alteration of these enzymatic activities can change the course or dictate the outcome of several pathophysiological events, including cancer, autoimmune and inflammatory diseases, infections, atherosclerosis, and ischemia-reperfusion injury, suggesting that these ecto-enzymes represent novel therapeutic targets for managing a variety of disorders.

Studies using tissues that overexpress CD73 and using CD73 knock-out mice have provided evidence that CD73 inhibitors have potential utility for melanomas, lung cancer, prostate cancer, and breast cancer (see, e.g., Sadej R. (2006) Melanoma Res 16:213-22). Because higher expression levels of CD73 are associated with tumor neovascularization, invasiveness, resistance to chemotherapy, and metastasis, CD73 inhibitors can be used to control tumor progression and metastasis. Other potential utilities are discussed elsewhere herein.

Although the compound of Formula (I) is believed to exert its activity by inhibition of CD73, a precise understanding of the compound's underlying mechanism of action is not required to practice the invention. For example, the compound can also exert its activity, at least in part, through modulation (e.g., inhibition) of other components of the purinergic signaling pathway (e.g., CD39). The purinergic signaling system consists of transporters, enzymes and receptors responsible for the synthesis, release, action, and extracellular inactivation of (primarily) ATP and its extracellular breakdown product adenosine (Sperlagh, B. et al. (December 2012) Neuropsychopharmacologia Hungarica 14(4):231-38). There are several potential opportunities for modulation of the signaling process. However, as will be apparent to the skilled artisan, some of these opportunities are more tractable than others.

Methods of Synthesis

In general, the compounds of Formula (I) are prepared using the methods described in, for example, WO 2017/120508.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Therapeutic and Prophylactic Uses

The present disclosure contemplates the use of oral formulations comprising a compound of Formula (I) and a chelating agent, as described herein in the treatment or prevention of a broad range of diseases, disorders and/or conditions, and/or the symptoms thereof. While particular uses are described in detail hereafter, it is to be understood that the present disclosure is not so limited. Furthermore, although general categories of particular diseases, disorders and conditions are set forth hereafter, some of the diseases, disorders and conditions may be a member of more than one category, and others may not be a member of any of the disclosed categories.

Oncology-related Disorders. In accordance with the present disclosure, an oral formulation comprising a compound of Formula (I) and a chelating agent can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The disclosure contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer is metastatic or at risk of becoming metastatic, or may occur in a diffuse tissue, including cancers of the blood or bone marrow (e.g., leukemia). In some further embodiments, the oral formulations described herein can be used to overcome T-cell tolerance. In one embodiment, the cancer is metastatic pancreatic adenocarcinoma.

In some embodiments, the present disclosure provides methods for treating a proliferative condition, cancer, tumor, or precancerous condition with the oral formulations described herein and at least one additional therapeutic or diagnostic agent, examples of which are set forth elsewhere herein.

In some embodiments, the methods described herein may be indicated as first line, second line or third line treatments.

Immune-related Disorders and Disorders with an Inflammatory Component. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the oral formulation comprising a compound of Formula (I) and a chelating agent described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The oral formulations described herein can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The oral formulations described herein can also be used to stimulate the immune system of patients suffering from iatrogenically-induced immune suppression, including those who have undergone bone marrow transplants, chemotherapy, or radiotherapy.

In particular embodiments of the present disclosure, the oral formulations described herein are used to increase or enhance an immune response to an antigen by providing adjuvant activity. In a particular embodiment, at least one antigen or vaccine is administered to a subject in combination with the oral formulations described herein to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with the oral formulations described herein.

Microbial-related Disorders. By inhibiting the immunosuppressive and anti-inflammatory activity of CD73, the present disclosure contemplates the use of an oral formulation comprising a compound of Formula (I) and a chelating agent described herein in the treatment and/or prevention of any viral, bacterial, fungal, parasitic or other infective disease, disorder or condition for which treatment with a CD73 inhibitor may be beneficial. Examples of such diseases and disorders include HIV and AIDS, staphylococcal and streptococcal infections (e.g., *Staphylococcus aureus* and *streptococcus sanguinis*, respectively), *leishmania, toxoplasma, trichomonas*, giardia, *Candida albicans, Bacillus anthracis*, and *Pseudomonas aeruginosa*. Oral formulations comprising a compound of Formula (I) and a chelating agent can be used to treat sepsis, decrease or inhibit bacterial growth, and reduce or inhibit inflammatory cytokines.

CNS-related and Neurological Disorders. Inhibition of CD73 may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Other Disorders. Embodiments of the present disclosure contemplate the administration of an oral formulation as described herein to a subject for the treatment or prevention of any other disorder that may benefit from at least some level of CD73 inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

In some embodiments, the oral formulations described herein may be used to inhibit statin-induced adenosine production, or reduce or decrease increases in blood glucose caused by a statin in a subject taking a statin (e.g., lovastatin and pravastatin)

Pharmaceutical Compositions

The oral formulation comprising a compound of Formula (I) and a chelating agent may be formulated as tablets, capsules, troches, lozenges, aqueous or oily suspensions, dispersible powders or granules, emulsions, hard or soft capsules, or syrups, solutions, microbeads, elixirs, or other forms suitable for oral use. These pharmaceutical compositions, comprising a compound of Formula (I), a chelating agent, and one or more pharmaceutically acceptable or physiologically acceptable diluents, carriers or excipients, may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of oral formulations. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions containing the oral formulation comprising a compound of Formula (I) and a chelating agent typically comprise one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

Combination Therapy

The present disclosure contemplates the use of an oral formulation comprising a compound of Formula (I) and a chelating agent alone or in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. The combination therapy may target different, but complementary mechanisms of action and thereby have a synergistic therapeutic or prophylactic effect on the underlying disease, disorder, or condition. In addition or alternatively, the combination therapy may allow for a dose reduction of one or more of the agents, thereby ameliorating, reducing or eliminating adverse effects associated with one or more of the agents.

The active therapeutic agents in such combination therapy can be formulated as a single composition or as separate compositions. If administered separately, each therapeutic agent in the combination can be given at or around the same time, or at different times. Furthermore, the therapeutic agents are administered "in combination" even if they have different forms of administration (e.g., oral capsule and intravenous), they are given at different dosing intervals, one therapeutic agent is given at a constant dosing regimen while another is titrated up, titrated down or discontinued, or each therapeutic agent in the combination is independently titrated up, titrated down, increased or decreased in dosage, or discontinued and/or resumed during a patient's course of therapy. If the combination is formulated as separate compositions, in some embodiments, the separate compositions are provided together in a kit.

In some embodiments, the additional therapeutic agent is an immunomodulatory agent. Suitable immunomodulatory agents that may be used in the present disclosure include CD40L, B7, and B7RP1; activating monoclonal antibodies (mAbs) to stimulatory receptors, such as, anti-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); indoleamine 2,3-dioxygenase 1 (IDO1) inhibitors and immune-stimulatory oligonucleotides.

In certain embodiments, the present disclosure provides methods for tumor suppression of tumor growth comprising administration of an oral formulation comprising a compound of Formula (I) and a chelating agent in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present disclosure include: (i) bcr/abl kinase inhibitors (e.g., GLEEVEC®); (ii) epidermal growth factor (EGF) receptor inhibitors, including kinase inhibitors and antibodies; (iii) her-2/neu receptor inhibitors (e.g., HERCEPTIN®); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in in immunomodulation can also be used in combination with an oral formulation comprising a compound of Formula (I) and a chelating agent described herein for the suppression of tumor growth in cancer patients.

In some embodiments, the additional therapeutic agent is a chemotherapeutic agent. Examples of chemotherapeutic agents include, but are not limited to, alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab-paclitaxel and docetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; anthracyclines; and pharmaceutically acceptable salts, acids or derivatives of any of the above. In one embodiment, the oral formulation described herein is combined with docetaxel. In another embodiment, the oral formulation described herein is combined with paclitaxel. In one embodiment, the oral formulation according to this disclosure is combined with nab-paclitaxel. In another embodiment, the oral formulation according to this disclosure is combined with gemcitabine.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; anti-androgens, including for example, abiraterone, enzalutamide, apalutamide, darolutamide, flutamide, bicalutamide, nilutamide, leuprolide, and goserelin; and pharmaceutically acceptable salts, acids or derivatives of any of the above. In certain embodiments, combination therapy comprises a chemotherapy regimen that includes one or more chemotherapeutic agents. In certain embodiments, combination therapy comprises administration of a hormone or related hormonal agent.

Additional treatment modalities that may be used in combination with an oral formulation comprising the compound of Formula (I) and a chelating agent include radiotherapy, a monoclonal antibody against a tumor antigen, a complex of a monoclonal antibody and toxin, a T-cell adjuvant, bone marrow transplant, or antigen presenting cells (e.g., dendritic cell therapy), including TLR agonists which are used to stimulate such antigen presenting cells.

In certain embodiments, the present disclosure contemplates the use of an oral formulation comprising the compound of Formula (I) and a chelating agent in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

In certain embodiments, the present disclosure contemplates the use of an oral formulation comprising the compound of Formula (I) and a chelating agent in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

In certain embodiments, the present disclosure contemplates the use of an oral formulation comprising the compound of Formula (I) and a chelating agent in combination with other agents that modulate the level of adenosine. Such therapeutic agents may act on the other ectonucleotides that catalyze the conversion of ATP to adenosine, including ectonucleoside triphosphate diphosphohydrolase 1 (ENTPD1, also known as CD39 or Cluster of Differentiation 39), which hydrolyzes ATP to ADP and ADP to AMP.

In some embodiments, this disclosure contemplates the use of an oral formulation comprising the compound of Formula (I) and a chelating agent in combination with other agents that target $A_{2A}$ and $A_{2B}$ receptors. Such therapeutic agents can be adenosine 2 receptor ($A_2R$) (e.g., $A_{2A}R$ and/or $A_{2B}R$) antagonists. Adenosine can bind to and activate four different G-protein coupled receptors: $A_1R$, $A_{2A}R$, $A_{2B}R$, and $A_3R$. The binding of adenosine to the $A_{2a}R$ receptor, which is expressed on T cells, natural killer cells and myeloid cells such as dendritic cells, leads to increased intracellular levels of cyclic AMP and the impairment of maturation and/or activation of such cells. This process significantly impairs the activation of the immune system against cancer cells. In addition, $A_{2A}R$ has been implicated in selectively enhancing anti-inflammatory cytokines, promoting the upregulation of PD-1 and CTLA-4, promoting the generation of LAG-3 and Foxp3+ regulatory T cells, and mediating the inhibition of regulatory T cells. PD-1, CTLA-4 and other immune checkpoints which are discussed further herein. Combining A2R antagonists in the combinations described herein may provide at least an additive effect. In one embodiment, the present disclosure contemplates the combination of an oral formulation according to this disclosure with the adenosine receptor antagonists described in WO 2018/136700, WO 2018/204661, WO 2018/213377, or WO/2020/102646. In one embodiment, the adenosine receptor antagonist is etrumadenant (AB928).

In certain embodiments, the present disclosure contemplates the use of an oral formulation comprising a compound of Formula (I) and a chelating agent in combination with inhibitors of phosphatidylinositol 3-kinases (PI3Ks), particularly the PI3Kγ isoform. PI3Kγ inhibitors can stimulate an anti-cancer immune response through the modulation of myeloid cells, such as by inhibiting suppressive myeloid cells, dampening immune-suppressive tumor-infiltrating macrophages or by stimulating macrophages and dendritic cells to make cytokines that contribute to effective T-cell responses leading to decreased cancer development and spread. In one embodiment, the PI3Kγ inhibitor is IPI-549. In another embodiment the PI3K inhibitor is chosen from those described in PCT/US2020/035920.

In certain embodiments, the present disclosure contemplates the use of an oral formulation comprising a compound of Formula (I) and a chelating agent with inhibitors of arginase, which has been shown to be either responsible for or to participate in inflammation-triggered immune dysfunction, tumor immune escape, immunosuppression and immunopathology of infectious disease. Exemplary arginase compounds can be found, for example, in PCT/US2019/020507 and WO/2020/102646.

In certain embodiments, the present disclosure contemplates the use of an oral formulation comprising a compound of Formula (I) and a chelating agent with inhibitors of HIF-2α, which plays an integral role in cellular response to low oxygen availability. Under hypoxic conditions, the hypoxia-inducible factor (HIF) transcription factors can activate the expression of genes that regulate metabolism, angiogenesis, cell proliferation and survival, immune evasion, and inflammatory response. HIF-2α overexpression has been associated with poor clinical outcomes in patients with various cancers; hypoxia is also prevalent in many acute and chronic inflammatory disorders, such as inflammatory bowel disease and rheumatoid arthritis.

The present disclosure also contemplates the combination of the oral formulations described herein with one or more RAS signaling inhibitors. Oncogenic mutations in the RAS family of genes, e.g., HRAS, KRAS, and NRAS, are associated with a variety of cancers. For example, mutations of G12C, G12D, G12V, G12A, G13D, Q61H, G13C and G12S, among others, in the KRAS family of genes have been observed in multiple tumor types. Direct and indirect inhibition strategies have been investigated for the inhibition of mutant RAS signaling. Indirect inhibitors target effectors other than RAS in the RAS signaling pathway, and include, but are not limited to, inhibitors of RAF, MEK, ERK, PI3K, PTEN, SOS (e.g., SOS1), mTORC1, SHP2 (PTPN11), and AKT. Non-limiting examples of indirect inhibitors under development include RMC-4630, RMC-5845, RMC-6291, RMC-6236, JAB-3068, JAB-3312, TNO155, RLY-1971, BI1701963. Direct inhibitors of RAS mutants have also been explored, and generally target the KRAS-GTP complex or the KRAS-GDP complex. Exemplary direct RAS inhibitors under development include, but are not limited to, sotorasib (AMG510), MRTX849, mRNA-5671 and ARS1620. In some embodiments, the one or more RAS signaling inhibitors are selected from the group consisting of RAF inhibitors, MEK inhibitors, ERK inhibitors, PI3K inhibitors, PTEN inhibitors, SOS1 inhibitors, mTORC1 inhibitors, SHP2 inhibitors, or AKT inhibitors. In other embodiments the one or more RAS signaling inhibitors directly inhibit RAS mutants.

Immune Checkpoint Inhibitors. The present disclosure contemplates the use of an oral formulation comprising a compound of Formula (I) and a chelating agent in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T-cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms.

In the clinical setting, the blockade of immune checkpoints which results in the amplification of antigen-specific T cell responses has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD-1 (programmed cell death protein 1); PD-L1 (PD-1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM domains); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present disclosure contemplates the use of an oral formulation comprising a compound of Formula (I) and a chelating agent in combination with inhibitors of the aforementioned immune-checkpoint receptors and ligands, as well as yet-to-be-described immune-checkpoint receptors and ligands. Certain modulators of immune checkpoints are currently approved, and many others are in development. When it was approved for the treatment of melanoma in 2011, the fully humanized CTLA4 monoclonal antibody ipilimumab (YERVOY®; Bristol-Myers Squibb) became the first immune checkpoint inhibitor to receive regulatory approval in the US. Fusion proteins comprising CTLA4 and an antibody (CTLA4-Ig; abatcept (ORENCIA®; Bristol-Myers Squibb)) have been used for the treatment of rheumatoid arthritis, and other fusion proteins have been shown to be effective in renal transplantation patients that are sensitized to Epstein Barr Virus. The next class of immune checkpoint inhibitors to receive regulatory approval were against PD-1 and its ligands PD-L1 and PD-L2. Approved anti-PD-1 antibodies include nivolumab (OPDIVO®; Bristol-Myers Squibb) and pembrolizumab (KEYTRUDA®; Merck) for various cancers, including squamous cell carcinoma, classical Hodgkin lymphoma and urothelial carcinoma. Approved anti-PD-L1 antibodies include avelumab (BAVENCIO®, EMD Serono & Pfizer), atezolizumab (TECENTRIQ®; Roche/Genentech), and durvalumab (IMFINZI®; AstraZeneca) for certain cancers, including urothelial carcinoma. While there are no approved therapeutics targeting TIGIT or its ligands CD155 and CD112, those in development include BMS-986207 (Bristol-Myers Squibb), MTIG7192A/RG6058 (Roche/Genentech), OMP-31M32 (OncoMed), and domvanalimab (AB154). Another approach to target the PD-1 receptor is the recombinant protein composed of the extracellular domain of PD-L2 (B7-DC) fused to the Fc portion of IgGI, called AMP-224.

In some combinations provided herein, the immune checkpoint inhibitor is selected from the group consisting of MEDI-0680, pidilizumab (CT-011), nivolumab, pembrolizumab, avelumab, atezolizumab, durvalumab, cemiplimab, sintilimab, tislelizumab, domvanalimab (AB154), and zimberelimab (AB122). In one embodiment, the immune checkpoint inhibitor is zimberelimab (AB122).

In one aspect of the present disclosure, the disclosed oral formulation comprising a compound of Formula (I) and a chelating agent are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD- L2), B7-H2 (ICOS-L), B7-H3, B7-H4, B7-H5 (VISTA), B7-H6, and B7-H7 (HHLA2). Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT13R, LIGHT, DcR3, HVEM, VEGI/TL1A, TRAMP/DR3, EDAR, EDA1, XEDAR, EDA2, TNFR1, Lymphotoxin a/TNF13, TNFR2, TNFa, LT13R, Lymphotoxin a 1132, FAS, FASL, RELT, DR6, TROY, NGFR.

In another aspect, the immuno-oncology agent is a cytokine that inhibits T cell activation (e.g., IL-6, IL-10, TGF-B, VEGF, and other immunosuppressive cytokines) or a cytokine that stimulates T cell activation, for stimulating an immune response.

In one aspect, T cell responses can be stimulated by a combination of an oral formulation comprising a compound of Formula (I) and a chelating agent and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with an oral formulation comprising a compound of Formula (I) and a chelating agent for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO11/107553, WO11/131407, WO13/87699, WO13/119716, WO13/132044) or FPA-008 (WO11/140249; WO13169264; WO14/036357).

In another aspect, the disclosed oral formulation comprising a compound of Formula (I) and a chelating agent can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The present disclosure encompasses pharmaceutically acceptable salts, acids or derivatives of any of the above.

Examples of therapeutic agents useful in combination therapy for the treatment of cardiovascular and/or metabolic-related diseases, disorders and conditions include statins (e.g., CRESTOR®, LESCOL®, LIPITOR®, MEVACOR®, PRAVACHOL®, and ZOCOR®), which inhibit the enzymatic synthesis of cholesterol; bile acid resins (e.g., COLESTID®, LO-CHOLEST, PREVALITE®, QUESTRAN®, and WELCHOL®), which sequester cholesterol and prevent its absorption; ezetimibe (ZETIA®), which blocks cholesterol absorption; fibric acid (e.g., TRICOR®), which reduces triglycerides and may modestly increase HDL; niacin (e.g., NIACOR®), which modestly lowers LDL cholesterol and triglycerides; and/or a combination of the aforementioned (e.g., VYTORIN® (ezetimibe with simvastatin). Alternative cholesterol treatments that may be candidates for use in combination with an oral formulation comprising a compound of Formula (I) and a chelating agent described herein include various supplements and herbs (e.g., garlic, policosanol, and guggul).

The present disclosure encompasses pharmaceutically acceptable salts, acids or derivatives of any of the above.

Examples of therapeutic agents useful in combination therapy for immune- and inflammatory-related diseases, disorders or conditions include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, flurofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required. Alternatively, the combination of the oral formulation according to this disclosure with a steroid can prevent or reduce adverse events such as, for example, autoimmune events.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE®, anti-TNF antibody fragments (e.g., CDP870), and soluble p55 or p75 TNF receptors, derivatives thereof, p75TNFRIgG (ENBREL®) or p55TNFR1gG (lenercept), soluble IL-13 receptor (sIL-13), and also TNFa-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with an oral formulation comprising the compound of Formula (I) and a chelating agent as described herein include interferon-131a (AVONEX®); interferon-131b (BETASERON®); copaxone; hyperbaric oxygen; intravenous immunoglobulin; clabribine; and antibodies to, or antagonists of, other human cytokines or growth factors (e.g., antibodies to CD40 ligand and CD80).

In still another embodiment, the disclosed oral formulation comprising a compound of Formula (I) and a chelating agent can be combined with an agent that inhibits tie CD47-SIRPα pathway. An example of an anti-CD47 antibody is magrolimab.

In another embodiment, combination of the disclosed oral formulation comprising a compound of Formula (I) and a chelating agent with an agent directed at Trop-2 is contemplated. Trop-2 antibody drug conjugates such as sacituzumab govitecan-hziy are known in the art.

In another embodiment, combination of the disclosed oral formulation comprising a compound of Formula (I) and a chelating agent with anti-VEGF such as bevacizumab is also contemplated.

Dosing

The oral formulation comprising a compound of Formula (I) and a chelating agent may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the compound of Formula (I) may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the compound of Formula (I) may be administered (e.g., orally) at dosage levels of about 0.01 mg/kg to about 50 mg/kg, or about 1 mg/kg to about 25 mg/kg, or about 1 mg/kg to about 10 mg/kg, or about 1 mg/kg to about 5 mg/kg of subject body weight per day, one or more times a day, to obtain the desired therapeutic effect.

In some embodiments, the compound of Formula (I) may be administered (e.g., orally) on a monthly, weekly or daily basis. In some embodiments, the compound of Formula (I) may be administered at least once a month, such as twice a month, three times a month, four times a month, once a week, or daily. In some embodiments, the compound of Formula (I) may be administered once every week, once every two weeks, once every 3 weeks, once every 4 weeks, once every 5 weeks, or once every 6 weeks. In certain embodiments, the compound of Formula (I) may be administered (e.g., orally) one or more times a day. In some embodiments, the compound of formula (I) may be administered (e.g., orally) 1, 2, or 3 times a day. In some embodiments, the compound of Formula (I) may be administered (e.g., orally) once a day.

For administration of an oral agent, the compositions can be provided in the form of tablets, capsules and the like containing from 1.0 to 1000 milligrams of the active ingredient, particularly 1, 3, 5, 10, 15, 20, 25, 50, 75, 100, 150, 200, 250, 300, 400, 500, 600, 750, 800, 900, and 1000 milligrams of the active ingredient. In some embodiments, the compositions contain from 25 milligrams to 350 milligrams of the active agent. In some embodiments, the compositions contain 50 milligrams. In some embodiments, the compositions contain 100 milligrams of the active agent. In some embodiments, the compositions contain 300 milligrams of the active agent.

In certain embodiments, the oral formulation comprising a compound of Formula (I) and a chelating agent is administered such that a dose of between 50 mg and 350 mg of the compound of Formula (I), such as 50 mg, 75 mg, 100 mg, 125 mg, 150 mg, 175 mg, 200 mg, 225 mg, 250 mg, 275 mg, 300 mg, 325 mg, or 350 mg is administered daily. In one embodiment, the oral formulation is administered such that a dose of 100 mg of the compound of Formula (I) is administered daily. In another embodiment, the oral formulation is administered such that a dose of 300 mg of the compound of Formula (I) is administered daily.

In certain embodiments, the dosage of the compound of Formula (I) is contained in a "unit dosage form". The phrase "unit dosage form" refers to physically discrete units, each unit containing a predetermined amount of the compound of Formula (I), either alone or in combination with one or more additional agents, sufficient to produce the desired effect. The predetermined amount of the compound of Formula (I) in the unit dosage form can be equal to the desired dosage, or a fraction thereof. For example, the unit dosage form can comprise the desired dose or ½, ⅓, ¼, ⅕, ⅙, ⅐, or ⅛ of the desired dose. In certain such embodiments, the unit dosage form can be administered 1, 2, 3, 4, 5, 6, 7 or 8 times, respectively, to achieve the desired dose of the active ingredient. In one or more embodiments, the predetermined amount of the compound of Formula (I) in the unit dosage form is equal to or is ½ of the desired dose. In certain such embodiments, the unit dosage form is administered 1 or 2 times, respectively, to achieve the desired dose of the active ingredient. It will be appreciated that the parameters of a unit dosage form will depend on the particular agent and the effect to be achieved.

Kits

The present disclosure also contemplates kits comprising an oral formulation comprising a compound of Formula (I) and a chelating agent, and pharmaceutical compositions thereof. The kits are generally in the form of a physical structure housing various components, as described below, and may be utilized, for example, in practicing the methods described above.

A kit can include an oral formulation comprising a compound of Formula (I) and a chelating agent disclosed herein (provided in, e.g., a sterile container), which may be in the form of a pharmaceutical composition suitable for administration to a subject. The oral formulation comprising a compound of Formula (I) and a chelating agent can be provided in a form that is ready for use (e.g., a tablet or capsule) or in a form requiring, for example, reconstitution or dilution (e.g., a powder) prior to administration. When the oral formulation comprising a compound of Formula (I) and a chelating agent is in a form that needs to be reconstituted or diluted by a user, the kit may also include diluents (e.g., sterile water), buffers, pharmaceutically acceptable excipients, and the like, packaged with or separately from the other components. When combination therapy is contemplated, the kit may contain the several agents separately or they may already be combined in the kit. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g., amounts, temperature, etc.), but some experimental errors and deviations should be accounted for.

EXAMPLES

Example 1: Oral Bioavailability of Compound (Ia), Compound 2 and Compound 3 is Improved Using Calcium Chelating Excipients Oral Formulations of Compound (Ia), Compound 2 and Compound 3

The influence of different excipients on the bioavailability of Compound (Ia), Compound 2 and Compound 3 in cynomolgus monkeys was investigated. The excipients tested were sodium phytate, sodium citrate, sodium EDTA, cyclodextrin, sodium taurocholate, sodium polystyrene sulfate, sodium caprate, sodium phosphate, carbomer 971P and palmitoyl carnitine chloride. Generally, an appropriate quantity (as indicated in Table 1) of Compound (Ia), Compound 2 or Compound 3 and an excipient were mixed to homogeneity and transferred to capsules for dosing. In one example, Compound (Ia) (500 mg assay, 1.063 correction factor applied for to account for purity) and 2.75 g of sodium phytate (Sigma) were combined in a mortar and pestle. The mixture was ground to homogeneity then 530 mg of the white powder was transferred to enteric capsules (Size 0) prior to dosing.

Dosing and Sample Collection

Male cynomolgus monkey, 2-4 kg and 2-5 years of age, were fasted overnight prior to each dose administration through approximately 4 hours post-dose. Compound (Ia), Compound 2 or Compound 3, either alone, or with excipient, in an enteric capsule was administered via an oral pet piller. Blood samples were collected from a peripheral vessel at designated time points, and centrifuged to obtain plasma.

Plasma Sample Preparation

Plasma samples obtained at each time point from the subjects were prepared by protein precipitation. An aliquot of 50 μL sample was added with 150 μL acetonitrile containing an internal standard ([[[(2R,3S,4R,5R)-5-[6-chloro-4-[[(1S)-2,2,2-trideuterio-1-(2-fluorophenyl)ethyl]amino]

pyrazolo[3,4-b]pyridin-1-yl]-3,4-dihydroxyoxolan-2-yl]-dideuteriomethoxy]-hydroxyphosphoryl]methylphosphonic acid, 200 ng/mL in Acetonitrile). The mixture was vortexed for 15 min and then centrifuged at 4500 rpm for 15 min at 4° C. (Sorvall Legend XTR centrifuge, Thermo Scientific, Langenselbold, Germany). 80 μL of the resulting supernatant was transferred into a new plate and mixed with 160 μL water followed by LC-MS/MS analysis. The results are summarized in Tables 1-3 below.

Bioanalytical Condition
Instrument:
 API 4000 mass spectrometer (Applied Biosystems, Foster City, Calif.)
 Shimadzu Nexera X$^2$ UHPLC System (Shimadzu Scientific Instruments, Canby, Oreg.)
Column: SHISEIDO CAPCELL PAK INERT ADME S3 (2.00 mm×50 mm, Part No. 79001)
Mobile Phase A: 8.6 mM Triethylamine, 100 mM HFIP (1,1,1,3,3,3-Hexafluoro-2-propanol) in Water
Mobile Phase B: 8.6 mM Triethylamine, and 100 mM HFIP in [Acetonitrile:water (95:5, v/v)
Needle wash (weak & strong): Acetone:MeCN:Water (80:20:20, v/v/v)
Flow Rate: 0.50 mL/min
HPLC Gradient:

| Time (min) | Mobile Phase A % | Mobile Phase B % |
|---|---|---|
| 0.5 | 98 | 2 |
| 1.5 | 30 | 70 |
| 2.00 | 0 | 100 |
| 2.40 | 0 | 100 |
| 2.41 | 98 | 2 |
| 2.61 | 0 | 100 |
| 2.81 | 98 | 2 |
| 3.01 | 0 | 100 |
| 3.21 | 98 | 2 |
| 3.41 | 0 | 100 |
| 3.61 | 98 | 2 |
| 3.81 | 0 | 100 |
| 4.01 | 98 | 2 |
| 4.5 | Stop | |

Ionization Mode: Electrospray (ESI)
Detection Mode: Negative MRM (Q1/Q3 transitions: m/z 579.0/157.0 for Compound (Ia) or Compound 3; m/z 584.0/157.0 for Internal Standard); (Q1/Q3 transitions m/z 562.2/157.0 for Compound 2; m/z 584.0/157.0 for Internal Standard)

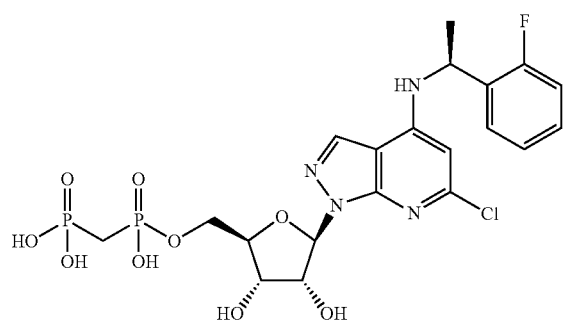

Compound (Ia)

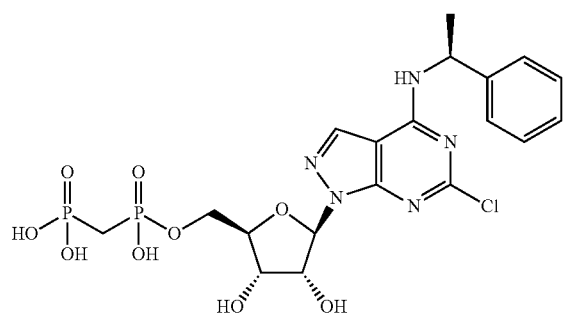

Compound 2

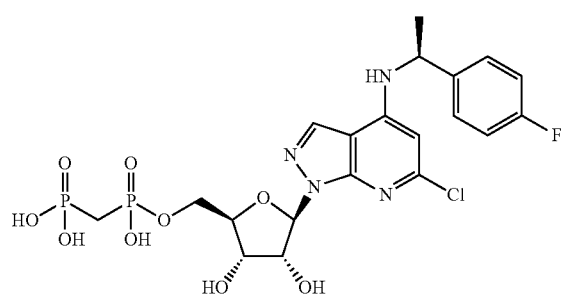

Compound 3

TABLE 1

Oral exposure of representative compounds when administered alone or with selected excipients to cynomolgus monkeys in capsules.

| Compound ID | Formulation[a] | Capsule | Dose (mg) | $C_{max}$ (ng/mL) | $AUC_{0-\infty}$ (h*ng/mL) | Exposure Enhancement |
|---|---|---|---|---|---|---|
| Ia (•3Na) | (neat) | Enteric | 50 | 631 | 13,400 | — |
| Ia (•3Na) | 275 mg sodium phytate (Sigma-Aldrich)[d] | Enteric | 50 | 3,680 | 122,000 | 9.1-fold[b] |
| Ia (•3Na) | 275 mg sodium phytate, hexasodium | Enteric | 50 | 4,440 | 152,000 | 11.4-fold[b] |
| Ia (•3Na) | 275 mg sodium phytate, dodecasodium | Enteric | 50 | 2,970 | 69,400 | 5.2-fold[b] |
| Ia ( 3Na) | 195 mg sodium citrate, 6 mg sodium dodecyl sulfate (SDS) | Enteric | 50 | 1,520 | 38,300 | 2.9-fold[b] |
| Ia ( 3Na) | 195 mg sodium citrate, 3 mg SDS | Enteric | 50 | 922 | 22,197 | 1.7-fold |

TABLE 1-continued

Oral exposure of representative compounds when administered alone or with selected excipients to cynomolgus monkeys in capsules.

| Compound ID | Formulation[a] | Capsule | Dose (mg) | $C_{max}$ (ng/mL) | $AUC_{0-\infty}$ (h*ng/mL) | Exposure Enhancement |
|---|---|---|---|---|---|---|
| Ia (3Na) | 195 mg sodium citrate, 6 mg SDS | Enteric | 10 | 286 | 1,940 | -- |
| Ia (3Na) | 195 mg sodium citrate, 6 mg SDS (non-fasted animal) | Enteric | 50 | 863 | 16,500 | 1.2-fold[b] |
| Ia (3Na) | 275 mg sodium phytate (Sigma-Aldrich)[d] | Enteric | 50 | 3,570 | 109,000 | 8.1-fold[b] |
| Ia (3Na) | 275 mg sodium phytate (Sigma-Aldrich)[d] | Enteric | 100 | 5,760 | 237,000 | -- |
| Ia (Neutral) | 275 mg sodium phytate (Sigma-Aldrich)[d] | Enteric | 50 | 2,790 | 102,000 | 7.6-fold[b] |
| Ia (3Na) | 50 mg sodium phytate (Sigma-Aldrich)[d] | Enteric | 50 | 1,650 | 59,700 | 4.5-fold[b] |
| Ia (3Na) | 100 mg Na-EDTA | Enteric | 50 | 6,840 | 154,000 | 11.5-fold[b] |
| Ia (3Na) | 100 mg cyclodextrin | Enteric | 50 | 526 | 8,230 | |
| Ia (3Na) | 25 mg sodium taurocholate | Enteric | 50 | 455 | 9,300 | -- |
| Ia (3Na) | 325 mg sodium polystyrene sulfate | Enteric | 50 | 1,420 | 41,350 | 3.1-fold[b] |
| Ia (3Na) | 227.5 mg sodium caprate | Enteric | 50 | 912 | 20,300 | 1.5-fold[b] |
| Ia (3Na) | 400 mg sodium phosphate | Enteric | 50 | 700 | 20,500 | 1.9-fold[b] |
| Ia (3Na) | 7% w/w carbomer 971P | Enteric | 50 | 1,480 | 41,300 | 3.1-fold[b] |
| Ia (3Na) | 100 mg palmitoyl carnitine chloride | Enteric | 50 | 3,660 | 43,400 | 3.2-fold[b] |
| 2 (Na) | (neat) | Enteric | 10 | 161 | 918 | |
| 2 (Na) | 195 mg sodium citrate | Enteric | 10 | 791 | 8,835 | 9.6-fold[e] |
| 2 (Na) | 275 mg sodium phytate (Sigma-Aldrich)[d] | Enteric | 10 | 824 | 6,013 | 6.6-fold[e] |
| 2 (Na) | 195 mg sodium citrate, 3 mg SDS | Enteric | 10 | 997 | 4,877 | 5.3-fold[e] |
| 2 (Na) | 275 mg sodium phytate (Sigma-Aldrich)[d] | Enteric | 50 | 2,323 | 104,865 | -- |
| 2 (Neutral) | 195 mg sodium citrate, 6 mg SDS | Gelatin | 50 | 3,180 | 151,000 | -- |
| 2 (Neutral) | 195 mg sodium citrate, 6 mg SDS | Enteric | 50 | 3,140 | 129,000 | -- |
| 2 (Na) | 195 mg sodium citrate, 3 mg SDS | Enteric | 50 | 2,530 | 67,133 | -- |
| 3 (3Na) | 195 mg sodium citrate, 3 mg SDS | Enteric | 50 | 1,320 | 38,733 | -- |
| 3 (3Na) | 275 mg sodium phytate (Sigma-Aldrich)[d] | Enteric | 50 | 3,550 | 149,333 | -- |

[a]Animals are fasted unless otherwise specified.
[b]Exposure enhancement relative to 50 mg Ia (3Na) without absorption enhancer.
[c]Exposure enhancement relative to 10 mg dose of 2(Na) without absorption enhancer.
[d]Contains ≥5 mol sodium/mol.

TABLE 2

Comparison of oral exposure of Compound (Ia) (3Na) administered neat versus administered with 275 mg sodium phytate in cynomolgus monkeys in enteric capsules.

| Formulation | Dose (mg) | $T_{max}$ (h) | $C_{max}$ (ng/mL) | $AUC_{last}$ (h*ng/mL) | $AUC_{0-\infty}$ (h*ng/mL) | $MRT_{0-\infty}$ (h) | Exposure Enhancement |
|---|---|---|---|---|---|---|---|
| Compound (Ia) (3Na) (+ 275 mg sodium phytate) | 50 | 3 | 3,680 | 88,000 | 122,000 | 35.8 | 9.1-fold |

TABLE 2-continued

Comparison of oral exposure of Compound (Ia) (3Na) administered neat versus administered with 275 mg sodium phytate in cynomolgus monkeys in enteric capsules.

| Formulation | Dose (mg) | $T_{max}$ (h) | $C_{max}$ (ng/mL) | $AUC_{last}$ (h*ng/mL) | $AUC_{0-\infty}$ (h*ng/mL) | $MRT_{0-\infty}$ (h) | Exposure Enhancement |
|---|---|---|---|---|---|---|---|
| Compound (Ia) (3Na) (neat) | 50 | 1.75 | 631 | 10,300 | 13,400 | 29.2 | — |

TABLE 3

Oral exposure of representative compounds when dosed with 195 mg trisodium citrate and 3 mg SDS to cynomolgus monkeys in enteric capsules.

| Compound ID | Dose (mg) | $C_{max}$ (ng/mL) | $AUC_{0-\infty}$ (h*ng/mL) |
|---|---|---|---|
| Ia | 50 | 922 | 22,197 |
| 2 | 50 | 2,530 | 67,133 |
| 3 | 50 | 1,320 | 38,733 |

TABLE 4

Oral exposure of representative compounds when dosed with 275 mg sodium phytate to cynomolgus monkeys in enteric capsules.

| Compound ID | Dose (mg) | $C_{max}$ (ng/mL) | $AUC_{0-\infty}$ (h*ng/mL) |
|---|---|---|---|
| Ia | 50 | 3,680 | 122,000 |
| 2 | 50 | 2,323 | 104,865 |
| 3 | 50 | 3,550 | 149,333 |

Example 2: Oral Bioavailability of Compound 2 is Improved Using Calcium Chelating Excipients (Dosing 10-30 mg/kg Compound 2+Excipient in Water at pH 8 Via Oral Gavage-5 mL/Kg in SD Rats)

Oral Formulations of Compound 2

The influence of different excipients on the bioavailability of Compound 2 was investigated in Sprague Dawley rats. The excipients tested were Solutol HS 15, soy L-α-phosphatidylcholine, trisodium citrate, sodium caprate, disodium EDTA, and sodium phytate. Generally, 10-30 mg of Compound 2 and the indicated quantity (Table 5) of excipient was combined and dissolved in 5 mL water. The pH was adjusted to a pH of 8 using HCl or NaOH as needed.

Dosing and Sample Collection

Male Sprague-Dawley rats, weighing between 0.27 to 0.32 kg, were fasted overnight prior to dose administration through approximately 4 hours post-dose. Compound 2 was administered orally by orogastric gavage at 5 mL/kg. Blood samples were collected via femoral vein at designated time points, and centrifuged to obtain plasma.

Plasma Sample Preparation

Plasma samples obtained at each time point from the subjects were prepared by protein precipitation. An aliquot of 50 μL sample was added with 150 μL acetonitrile containing an internal standard ([[(2R,3S,4R,5R)-5-[2-chloro-6-(cyclopentylmethylamino)purin-9-yl]-3,4-dihydroxyoxolan-2-yl]methoxymethylphosphonic acid, 200 ng/mL in Acetonitrile). The mixture was vortexed for 15 min and then centrifuged at 4500 rpm for 15 min at 4° C. (Sorvall Legend XTR centrifuge, Thermo Scientific, Langenselbold, Germany). 80 μL of the resulting supernatant was transferred into a new plate and mixed with 160 μL water followed by LC-MS/MS analysis. The results are summarized in Table 5 below.

Bioanalytical Condition

Instrument:
  API 4000 mass spectrometer (Applied Biosystems, Foster City, Calif.)
  Shimadzu Nexera $X^2$ UHPLC System (Shimadzu Scientific Instruments, Canby, Oreg.)
Column: SHISEIDO CAPCELL PAK INERT ADME S3 (2.00 mm×50 mm, Part No. 79001)
Mobile Phase A: 8.6 mM Triethylamine, 100 mM HFIP (1,1,1,3,3,3-Hexafluoro-2-propanol) in Water
Mobile Phase B: 8.6 mM Triethylamine, and 100 mM HFIP in [Acetonitrile:water (95:5, v/v) Needle wash (weak & strong): Acetone: MeCN: Water (80:20:20, v/v/v) Flow Rate: 0.50 mL/min
HPLC Gradient:

| Time (min) | Mobile Phase A % | Mobile Phase B % |
|---|---|---|
| 0.5 | 98 | 2 |
| 1.5 | 30 | 70 |
| 2.00 | 0 | 100 |
| 2.40 | 0 | 100 |
| 2.41 | 98 | 2 |
| 2.61 | 0 | 100 |
| 2.81 | 98 | 2 |
| 3.01 | 0 | 100 |
| 3.21 | 98 | 2 |
| 3.41 | 0 | 100 |
| 3.61 | 98 | 2 |
| 3.81 | 0 | 100 |
| 4.01 | 98 | 2 |
| 4.5 | Stop | |

Ionization Mode: Electrospray (ESI)
Detection Mode: Negative MRM (Q1/Q3 transitions: m/z 562.2/157.0 for Compound 2; m/z 584.0/157.0 for Internal Standard)

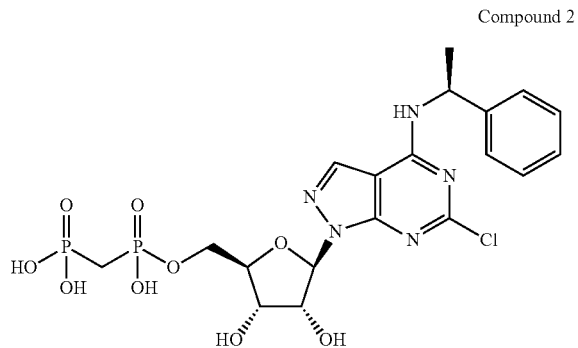 [SMILES: C[C@H](Nc1nc(Cl)nc2c1cnn2[C@@H]1O[C@H](COP(=O)(O)CP(=O)(O)O)[C@@H](O)[C@H]1O)c1ccccc1]

Compound 2

TABLE 5

Oral exposure of Compound 2 when administered alone or with selected excipients to male Sprague-Dawley rats.

| Compound 2 (mg/kg) | Excipient (mg/kg) | Bioavailability (% F) |
|---|---|---|
| 30 | None | 0.03 |
| 30 | Solutol HS 15, 1,500 | 0.015 |
| 30 | Soy L-α-phosphatidylcholine 150 mg | 0.07 |
| 30 | Trisodium citrate 20 mg | 0.10 |
| 30 | Trisodium citrate 64.5 mg | 0.60 |
| 10 | Trisodium citrate 64.5 mg/sodium caprate 49 mg | 0.23 |
| 30 | Disodium EDTA 5 mg | 0.60 |
| 30 | Disodium EDTA 20 mg | 2.8 |
| 10 | Sodium phytate (Sigma)[a] 165 mg | 2.3 |
| 10 | Sodium phytate (Sigma)[a] 165 mg/SDS 2 mg | 2.0 |

[a]Contains ≥5 mol sodium/mol.

Particular embodiments of this invention are described herein, including the best mode known to the inventors for carrying out the invention. The invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. An oral formulation comprising a compound of Formula (I) or a pharmaceutically acceptable salt, hydrate or solvate thereof, and inositol hexaphosphate or an ionized salt thereof, wherein the compound of Formula (I) has the structure:

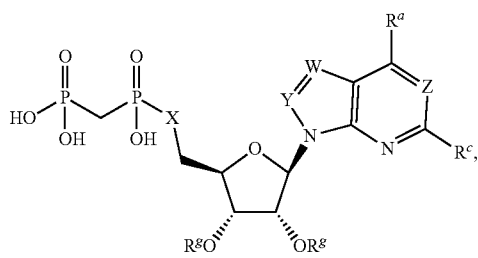

wherein,
W is selected from the group consisting of $CR^e$ and N;
X is selected from the group consisting of O, $CH_2$, and S;
each of Y and Z is independently selected from the group consisting of CH and N:
$R^g$ is H or the two $R^g$ groups are combined to form an acetonide;
$R^a$ is selected from the group consisting of $NH_2$, $NHR^1$, and $NR^1R^2$;
$R^c$ is selected from the group consisting of H, halogen, haloalkyl, $NH_2$, $NHR^3$, $NR^3R^4$, $R^3$, OH, $OR^3$, $SR^3$, $SO_2R^3$, $-X^1-NH_2$, $-X^1-NHR^3$, $-X^1-NR^3R^4$, $-X^1-OH$, $-X^1-OR^3$, $-X^1-SR^3$, and $-X^1-SO_2R^3$;

$R^e$ is selected from the group consisting of H, halogen, and optionally substituted $C_1$-$C_6$ alkyl;

each $X^1$ is $C_1$-$C_4$alkylene; and each $R^1$, $R^2$, $R^3$, and $R^4$ is independently selected from the group consisting of optionally substituted $C_1$-$C_{10}$ alkyl, optionally substituted $C_3$-$C_7$ cycloalkyl, optionally substituted $C_3$-$C_7$ cycloalkyl$C_1$-$C_4$alkyl-, optionally substituted 4-7 membered heterocycloalkyl, optionally substituted 4-7 membered heterocycloalkyl$C_1$-$C_4$alkyl-, optionally substituted aryl, optionally substituted aryl$C_1$-$C_4$alkyl-, optionally substituted heteroaryl, and optionally substituted heteroaryl$C_1$-$C_4$alkyl-, or when $R^1$ and $R^2$ or $R^3$ and $R^4$ are attached to the same nitrogen, they combine to form a 4- to 7-membered heterocyclic ring.

2. The oral formulation of claim 1, wherein X is O.

3. The oral formulation of claim 1, wherein $R^g$ is H.

4. The oral formulation of any one of claim 1, wherein $R^a$ is $NHR^1$ and $R^1$ is selected from the group consisting of optionally substituted aryl$C_1$-$C_4$alkyl- and optionally substituted heteroaryl$C_1$-$C_4$alkyl-.

5. The oral formulation of claim 1, wherein $R^a$ is $NHR^1$ and $R^1$ is optionally substituted aryl$C_1$-$C_4$alkyl-.

6. The oral formulation of claim 1, wherein $R^c$ is selected from the group consisting of H, halogen, and haloalkyl.

7. The oral formulation of claim 1, wherein $R^c$ is halogen.

8. The oral formulation of claim 1, wherein $R^e$ is H.

9. The oral formulation of claim 1, wherein the compound of Formula (I), or the pharmaceutically acceptable salt thereof, has a structure selected from the group consisting of

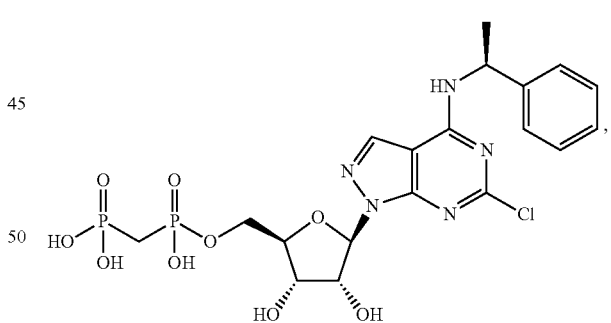

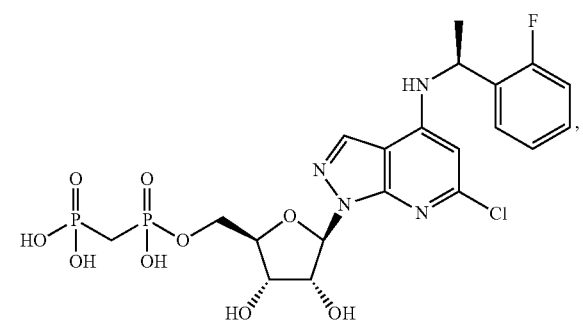 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

-continued

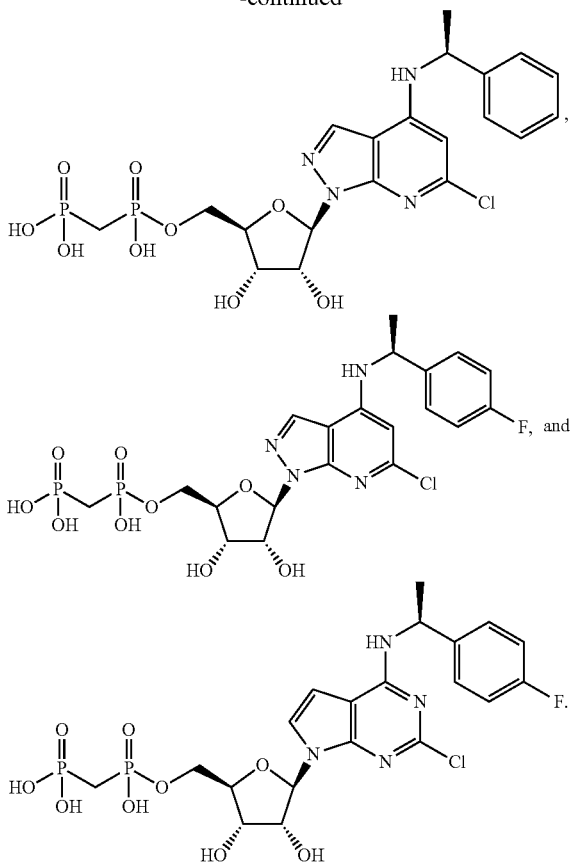

10. The oral formulation of claim 1, wherein the compound of Formula (I), or the pharmaceutically acceptable salt thereof, has the structure

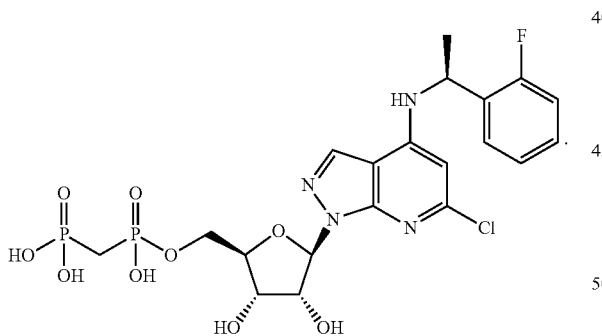

11. The oral formulation of claim 1, wherein, the inositol hexaphosphate or an ionized salt thereof is a partially ionized inositol hexaphosphate salt.

12. The oral formulation of claim 11, wherein the partially ionized inositol hexaphosphate salt is hexasodium inositol hexaphosphate.

13. The oral formulation of claim 11, wherein the partially ionized inositol hexaphosphate salt is an inositol hexaphosphate salt having not less than 5 mol sodium per mol of inositol phosphate.

14. The oral formulation of claim 11, wherein the partially ionized inositol hexaphosphate salt is an inositol hexaphosphate salt having not less than 4 mol sodium per mol of inositol phosphate.

15. The oral formulation of claim 11, wherein the partially ionized inositol hexaphosphate salt is an inositol hexaphosphate salt having not less than 3 mol sodium per mol of inositol phosphate.

16. The oral formulation of claim 11, wherein the partially ionized inositol hexaphosphate salt is an inositol hexaphosphate salt having not less than 2 mol sodium per mol of inositol phosphate.

17. The oral formulation of claim 1, wherein the inositol hexaphosphate or an ionized salt thereof is a fully ionized inositol hexaphosphate salt.

18. The oral formulation of claim 1, having a molar ratio of inositol hexaphosphate or an ionized salt thereof to compound of Formula (I) of from about 1:1 to 10:1.

19. The oral formulation of claim 18, wherein the ratio of inositol hexaphosphate or an ionized salt thereof to compound of Formula (I) is from about 3:1 to 10:1.

20. The oral formulation of claim 18, wherein the ratio of inositol hexaphosphate or an ionized salt thereof to compound of Formula (I) is from about 1:1 to 7:1.

21. The oral formulation of claim 19, wherein the ratio of inositol hexaphosphate or an ionized salt thereof to compound of Formula (I) is from about 1:1 to 5:1.

22. The oral formulation of claim 19, wherein the ratio of inositol hexaphosphate or an ionized salt thereof to compound of Formula (I) is about 3.5:1.

23. A method of treating a disease, disorder, or condition, mediated at least in part by CD73, the method comprising administering an oral formulation of claim 1 to a subject in need thereof.

24. An oral formulation comprising a compound of Formula (I) or a pharmaceutically acceptable salt, hydrate or solvate thereof, and edetic acid (EDTA) or an ionized salt thereof, wherein the compound of Formula (I) has the structure:

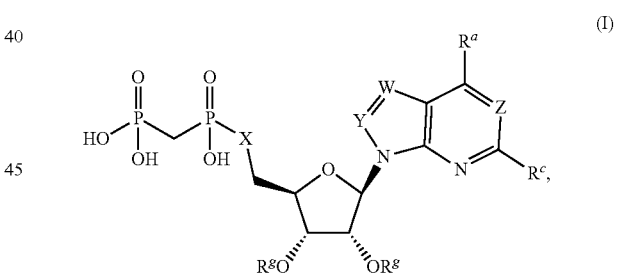

wherein,
W is selected from the group consisting of $CR^e$ and N;
X is selected from the group consisting of O, $CH_2$, and S;
each of Y and Z is independently selected from the group consisting of CH and N;
$R^g$ is H or the two $R^g$ groups are combined to form an acetonide;
$R^a$ is selected from the group consisting of $NH_2$, $NHR^1$, and $NR^1R^2$;
$R^c$ is selected from the group consisting of H, halogen, haloalkyl, $NH_2$, $NHR^3$, $NR^3R^4$, $R^3$, OH, $OR^3$, $SR^3$, $SO_2R^3$, —$X^1$—$NH_2$, —$X^1$—$NHR^3$, —$X^1$—$NR^3R^4$, —$X^1$—OH, —$X^1$—$OR^3$, —$X^1$—$SR^3$, and —$X^1$—$SO_2R^3$;
$R^e$ is selected from the group consisting of H, halogen, and optionally substituted $C_1$-$C_6$ alkyl;
each $X^1$ is $C_1$-$C_4$alkylene; and each $R^1$, $R^2$, $R^3$, and $R^4$ is independently selected from the group consisting of optionally substituted $C_1$-$C_{10}$ alkyl, optionally substituted $C_3$-$C_7$ cycloalkyl, optionally substituted $C_3$-$C_7$ cycloalkyl$C_1$-$C_4$alkyl-, optionally substituted 4-7 membered heterocycloalkyl, optionally substituted 4-7 membered heterocycloalkyl$C_1$-$C_4$alkyl-, optionally substituted aryl, optionally substituted aryl$C_1$-$C_4$alkyl-, optionally substituted heteroaryl, and optionally substituted heteroaryl$C_1$-$C_4$alkyl-, or when $R^1$ and $R^2$ or $R^3$ and $R^4$ are attached to the same nitrogen, they combine to form a 4- to 7-membered heterocyclic ring.

* * * * *

UNITED STATES PATENT AND TRADEMARK OFFICE
CERTIFICATE OF CORRECTION

PATENT NO. : 11,633,416 B1
APPLICATION NO. : 17/193473
DATED : April 25, 2023
INVENTOR(S) : Kenneth Victor Lawson et al.

It is certified that error appears in the above-identified patent and that said Letters Patent is hereby corrected as shown below:

In the Claims

In Claim 1, Column 43, Line 61, please replace "consisting of CH and N:" with --consisting of CH and N;--.

In Claim 1, Column 43, Line 62, please replace "$R^g$ is H or the two $R^9$ groups are combined to form an" with --$R^g$ is H or the two $R^g$ groups are combined to form an--.

In Claim 3, Column 44, Line 24, please replace "The oral formulation of claim 1, wherein $R^9$ is H." with --The oral formulation of claim 1, wherein $R^g$ is H.--.

In Claim 4, Column 44, Line 25, please replace "The oral formulation of any one of claim 1, wherein $R^a$ with --The oral formulation of claim 1, wherein $R^a$--.

In Claim 13, Column 45, Line 63, please replace "inositol phosphate" with --inositol hexaphosphate--.

In Claim 14, Column 45, Line 67, please replace "inositol phosphate" with --inositol hexaphosphate--.

In Claim 15, Column 46, Line 4, please replace "inositol phosphate" with --inositol hexaphosphate--.

In Claim 16, Column 46, Line 8, please replace "inositol phosphate" with --inositol hexaphosphate--.

In Claim 24, Column 46, Line 55, please replace "consisting of CH and N:" with --consisting of CH and N;--.

Signed and Sealed this
Fourth Day of July, 2023

*Katherine Kelly Vidal*

Katherine Kelly Vidal
*Director of the United States Patent and Trademark Office*